(12) United States Patent
Hane

(10) Patent No.: US 12,029,383 B2
(45) Date of Patent: Jul. 9, 2024

(54) STRESS ESTIMATION SYSTEM, STRESS ESTIMATION APPARATUS, ENDOSCOPE APPARATUS, AND STRESS ESTIMATION METHOD

(71) Applicant: OLYMPUS CORPORATION, Tokyo (JP)

(72) Inventor: Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 926 days.

(21) Appl. No.: 17/030,563

(22) Filed: Sep. 24, 2020

(65) Prior Publication Data

US 2021/0048355 A1 Feb. 18, 2021

Related U.S. Application Data

(63) Continuation of application No. PCT/JP2018/013671, filed on Mar. 30, 2018.

(51) Int. Cl.
*G01B 11/16* (2006.01)
*A61B 1/00* (2006.01)
(Continued)

(52) U.S. Cl.
CPC ...... *A61B 1/00006* (2013.01); *A61B 1/00097* (2022.02); *A61B 1/009* (2022.02);
(Continued)

(58) Field of Classification Search
CPC . A61B 1/00006; A61B 1/00097; A61B 1/009; A61B 2090/064; A61B 1/0051;
(Continued)

(56) References Cited

U.S. PATENT DOCUMENTS

2014/0094701 A1* 4/2014 Kwartowitz ......... A61B 8/5223
                                                          600/438
2014/0230562 A1* 8/2014 Yamamoto ............... G01N 3/20
(Continued)

FOREIGN PATENT DOCUMENTS

JP       H6-154153         6/1994
JP       H11178932 A   *   7/1999
(Continued)

OTHER PUBLICATIONS

JP-H11178932-A-translate (Year: 1997).*
(Continued)

*Primary Examiner* — Kristina M Deherrera
*Assistant Examiner* — Fatemeh Esfandiari Nia
(74) *Attorney, Agent, or Firm* — Scully, Scott, Murphy & Presser, P.C.

(57) ABSTRACT

A stress estimation system includes a flexible member with flexibility. The flexible member is to be inserted into an inside of an examined body and to apply force to an inner surface of the examined body. The stress estimation system also includes a force information acquisition unit configured to acquire force information relating to force acting on the flexible member, and a stress estimation unit configured to calculate information of stress relating to a stress estimation area, based on the force information.

16 Claims, 21 Drawing Sheets

(51) Int. Cl.
*A61B 1/005* (2006.01)
*G01B 11/24* (2006.01)
*G01D 5/20* (2006.01)
*G01L 1/24* (2006.01)
*G01N 3/08* (2006.01)
*G02B 23/24* (2006.01)
*A61B 90/00* (2016.01)
*G01L 5/16* (2020.01)

(52) U.S. Cl.
CPC .............. *G01B 11/18* (2013.01); *G01B 11/24* (2013.01); *G01D 5/20* (2013.01); *G01L 1/242* (2013.01); *G01N 3/08* (2013.01); *G02B 23/2476* (2013.01); *A61B 2090/064* (2016.02); *G01L 5/16* (2013.01)

(58) Field of Classification Search
CPC ............ A61B 5/065; A61B 2034/2051; A61B 2034/2061; A61B 2090/065; G01B 11/18; G01B 11/24; G01B 7/003; G01D 5/20; G01L 1/242; G01L 5/16; G02B 23/2476; G01N 3/08
USPC .......................................... 73/838, 849, 852
See application file for complete search history.

(56) References Cited

U.S. PATENT DOCUMENTS

| | | |
|---|---|---|
| 2015/0359419 A1 | 12/2015 | Hane et al. |
| 2017/0303769 A1 | 10/2017 | Ito et al. |

FOREIGN PATENT DOCUMENTS

| | | | |
|---|---|---|---|
| JP | 2007-185355 A | | 7/2007 |
| JP | 2008080021 A | * | 4/2008 |
| JP | 2009-522016 A | | 6/2009 |
| JP | 2013-94337 A | | 5/2013 |
| JP | 2014-161374 A | | 9/2014 |
| WO | 2016/121106 A1 | | 8/2016 |
| WO | 2016/189724 A1 | | 12/2016 |
| WO | 2017/009905 A1 | | 1/2017 |

OTHER PUBLICATIONS

JP-2008080021-A-Translate (Year: 2008).*
Chinese Office Action dated Mar. 1, 2023 received in 201880090745.8.
Japanese Office Action dated Jan. 4, 2022 received in 2020-508805.
Japanese Office Action dated Jun. 8, 2021 received in 2020-508805.
Uno Y. et al., "Colonic Perforation and Serosal Tears Associated With Colonoscopy", The Lancet 349(9069):1888 (Jun. 28, 1997).
International Search Report dated May 1, 2018 received in International Application No. PCT/JP2018/013671, together with an English-language translation.
English translation of International Preliminary Report on Patentability dated Oct. 15, 2020 together with the Written Opinion issued in International Application No. PCT/JP2018/013671.

* cited by examiner

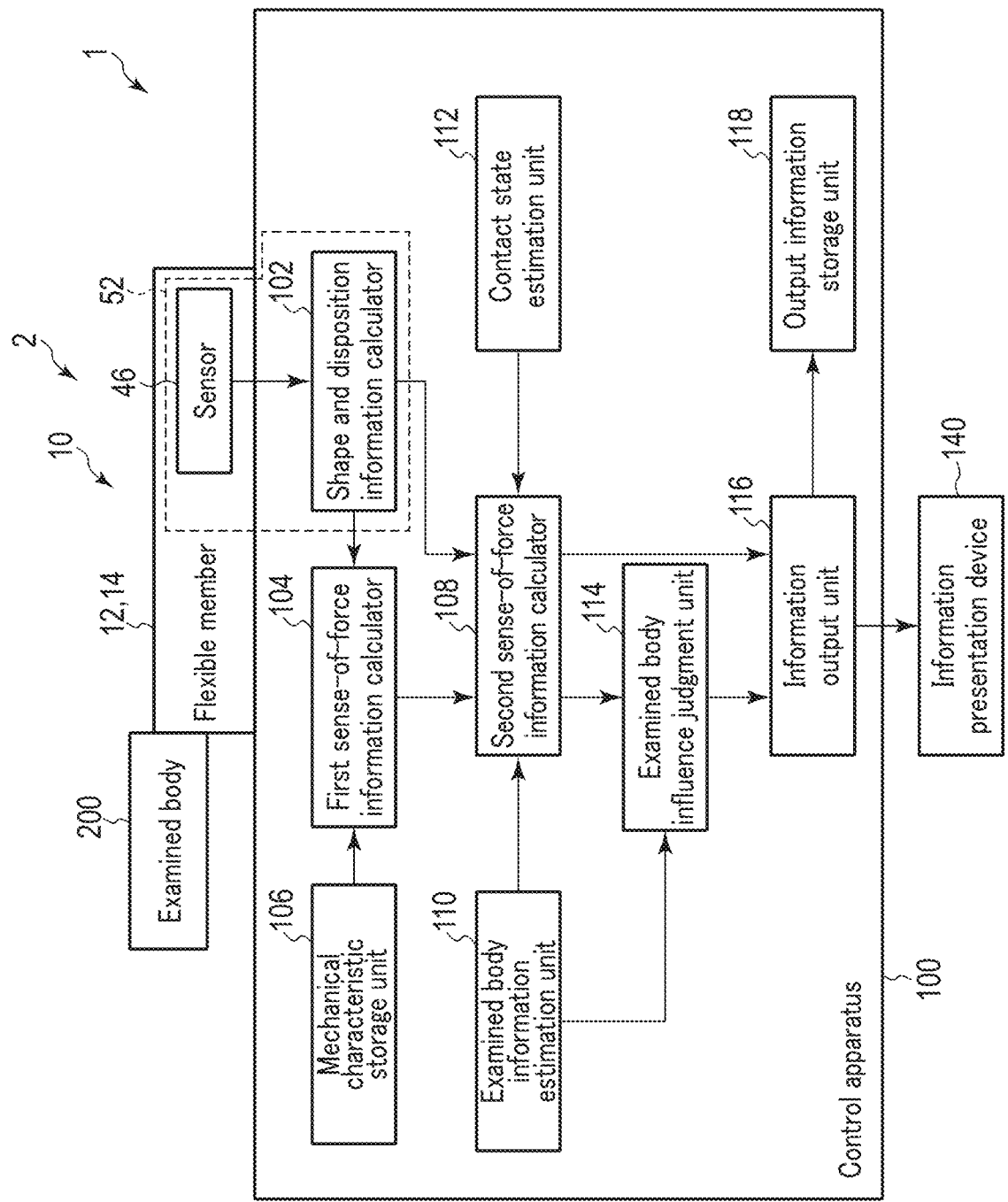
F I G. 1

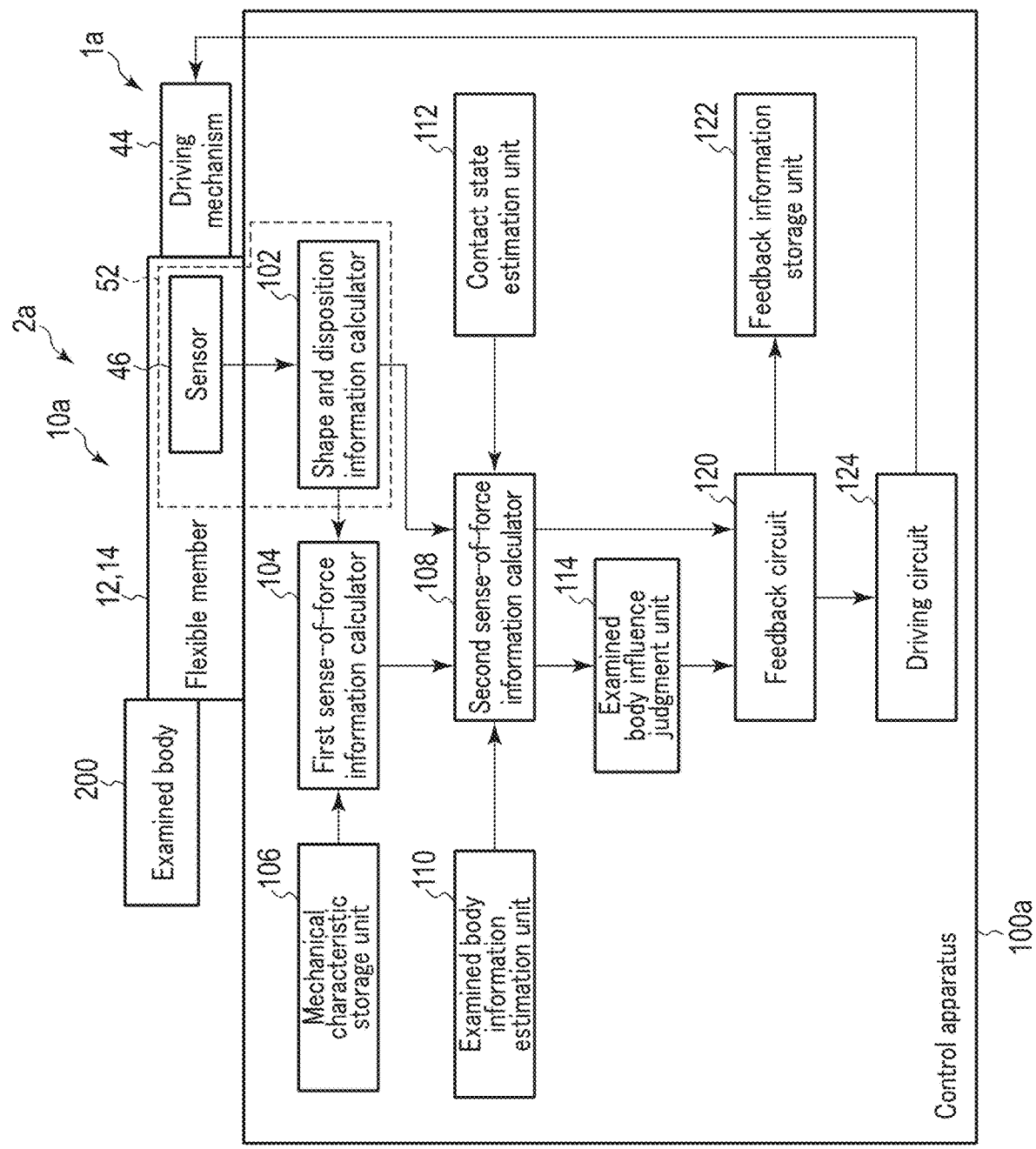
F I G. 21

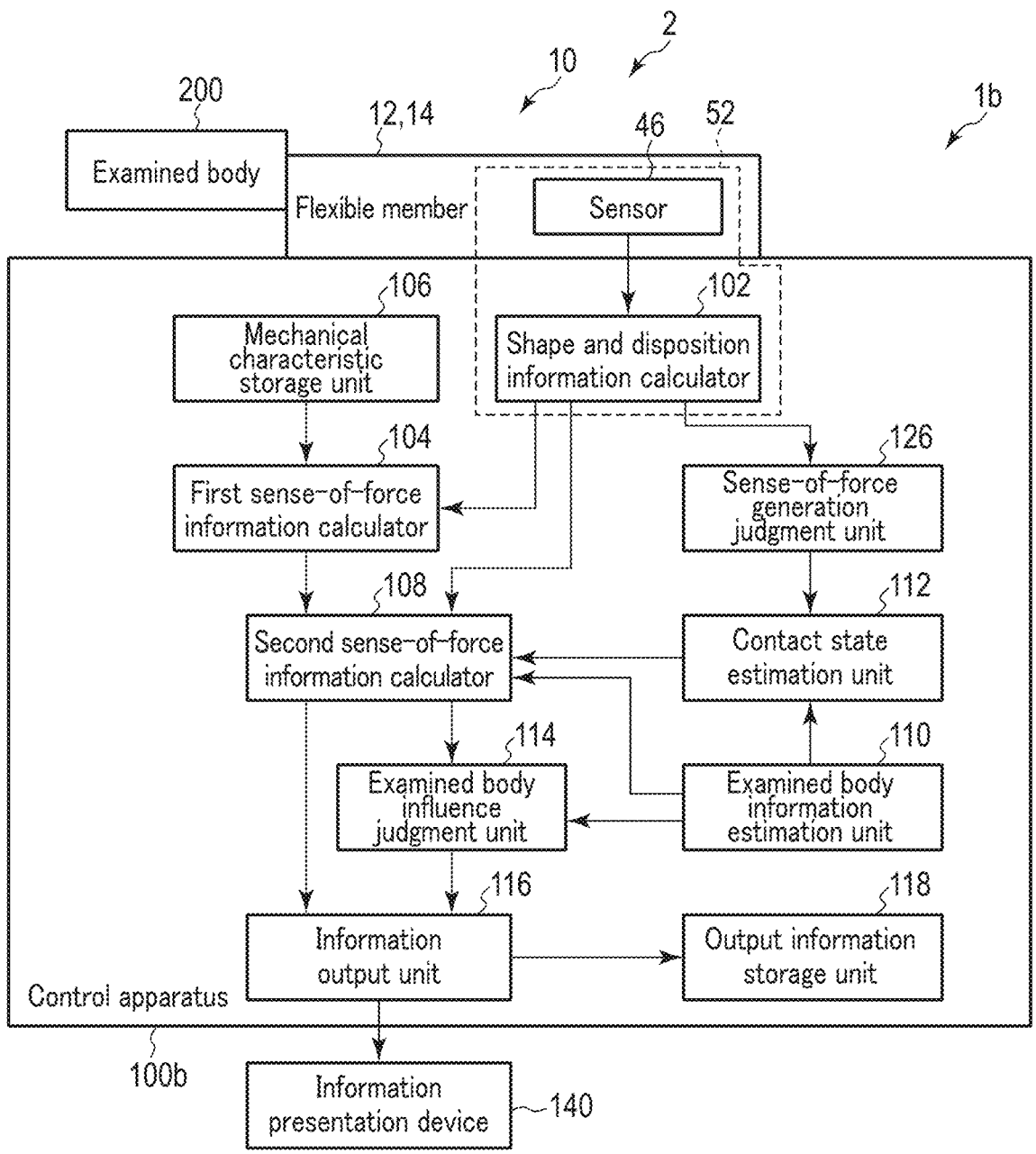
F I G. 23

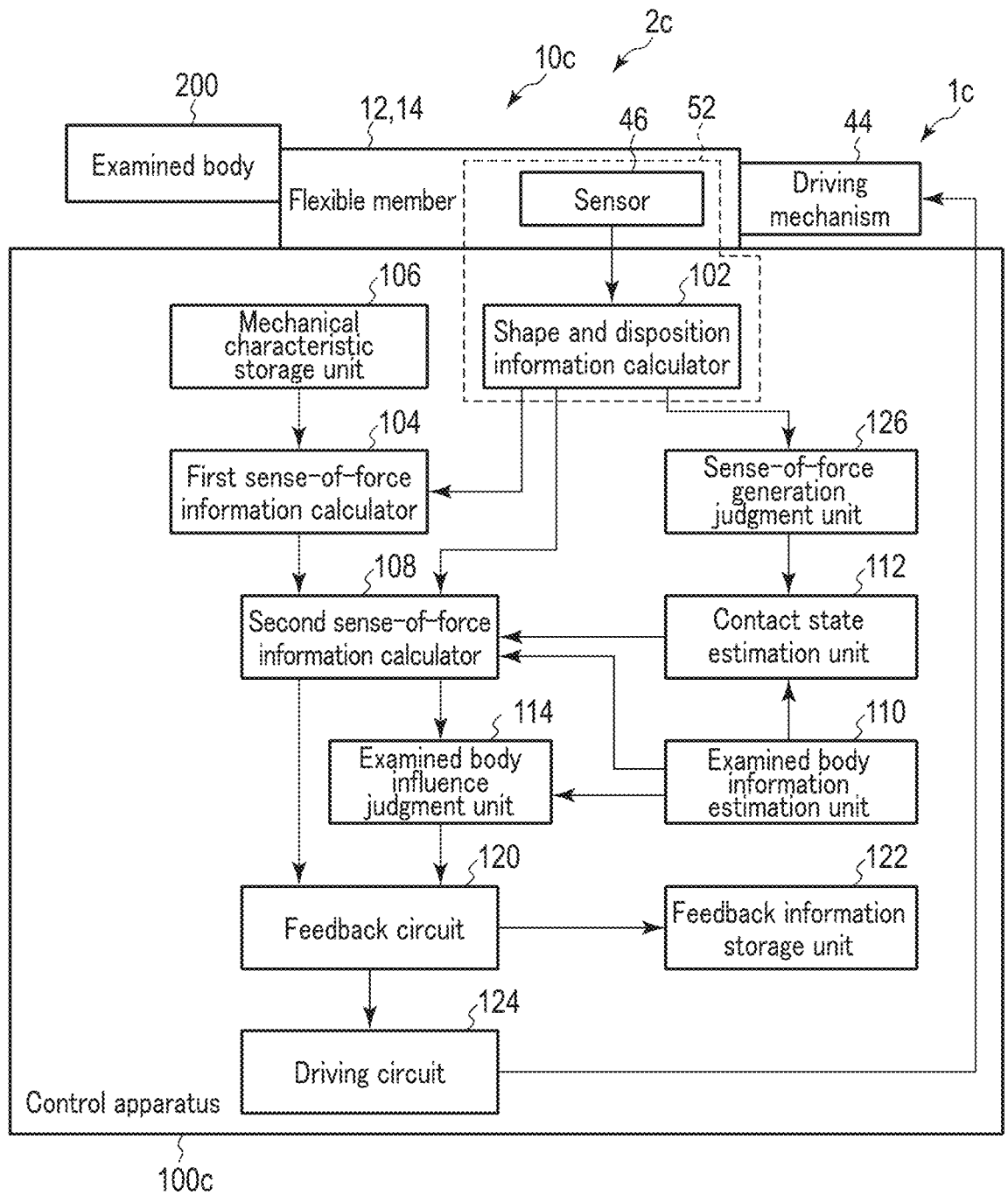
F I G. 24

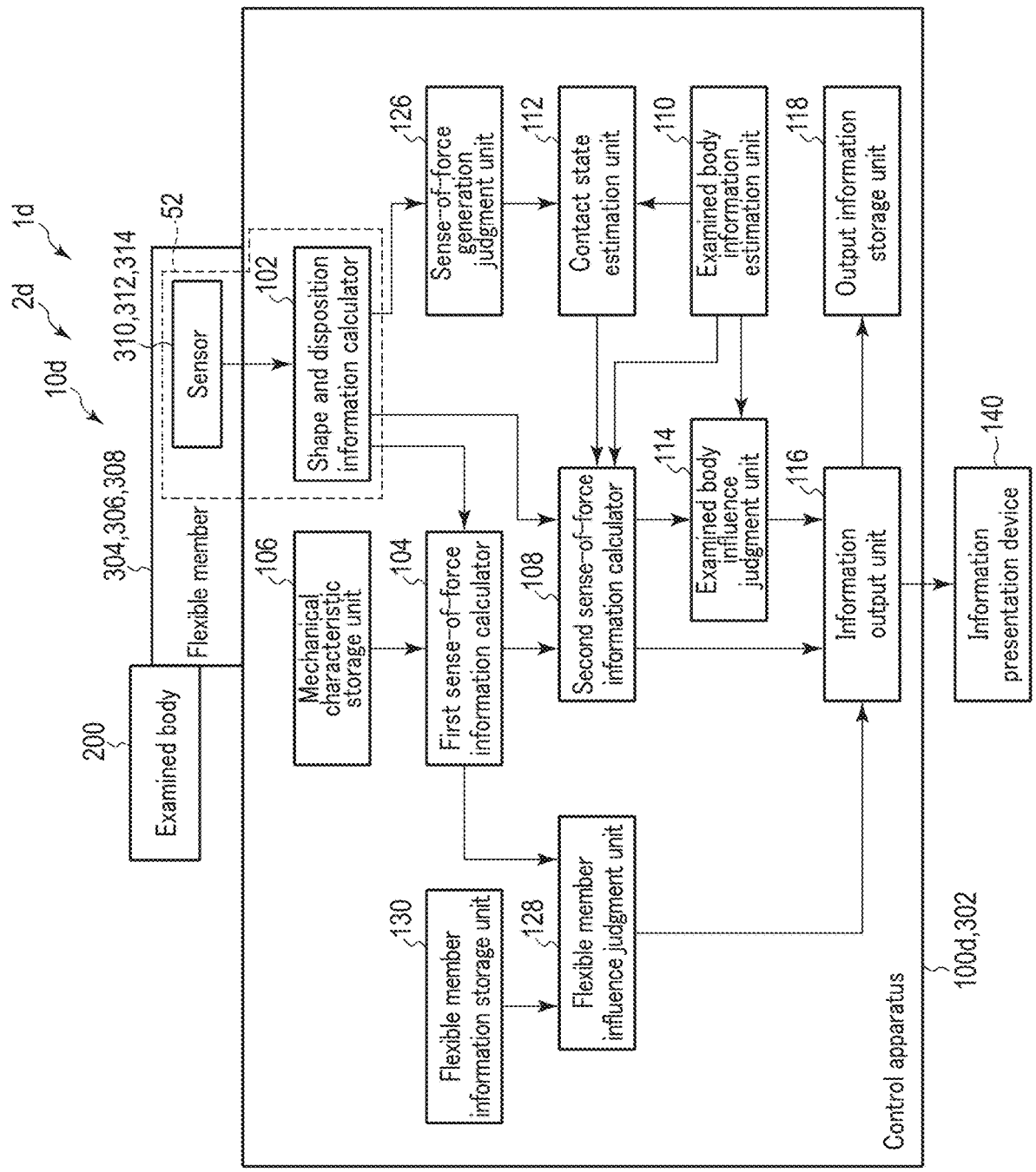
F I G. 26

STRESS ESTIMATION SYSTEM, STRESS ESTIMATION APPARATUS, ENDOSCOPE APPARATUS, AND STRESS ESTIMATION METHOD

CROSS-REFERENCE TO RELATED APPLICATIONS

This application is a Continuation Application of PCT Application No. PCT/JP2018/013671, filed Mar. 30, 2018, the entire contents of which are incorporated herein by reference.

BACKGROUND OF THE INVENTION

1. Field of the Invention

The present invention relates to a stress estimation system, a stress estimation apparatus, an endoscope apparatus, and a stress estimation method.

2. Description of the Related Art

When a flexible member, such as an insertion section of an endoscope or an arm of a small-diameter manipulator for medical use or industrial use, is inserted into an examined body, there is a case in which the flexible member comes in contact with the examined body and pushes the examined body. In order to estimate the influence on the examined body due to such pushing, it is known to calculate information of an external force acting on the flexible member.

For example, Jpn. PCT National Publication No. 2009-522016 discloses that an insertion section is provided with a strain gauge, and the amount of force, which is received from the examined body when the insertion section comes in contact with the surface of the examined body, is measured by the strain gauge. Jpn. Pat. Appln. KOKAI Publication. No. H6-154153 discloses a detection apparatus configured to detect the amount of force, which is received from an organ in a body cavity, by a pressure-sensitive sensor provided on a distal end of an insertion section of an endoscope. Jpn. Pat. Appln. KOKAI Publication No. 2013-094337 discloses that an insertion section is provided with a plurality of bend sensors, and operation support information including external force information relating to an external force acting on the insertion section is calculated by a combinational calculation of pieces of detection information of the bend sensors.

BRIEF SUMMARY OF THE INVENTION

A stress estimation system includes: a flexible member with flexibility, the flexible member being to be inserted into an inside of an examined body and to apply force to an inner surface of the examined body; a force information acquisition unit configured to acquire force information relating to force acting on the flexible member; and a stress estimation unit configured to calculate information of stress relating to a stress estimation area, based on the force information.

A stress estimation apparatus includes: a force information acquisition unit configured to acquire force information relating to force acting on a flexible member to apply force to an inner surface of an examined body; and a stress estimation unit configured to calculate information of stress relating to a stress estimation area, based on the force information.

An endoscope system includes: an endoscope insertion section with flexibility, the endoscope insertion section being to be inserted into an inside of an examined body and to apply force to an inner surface of the examined body; a force information acquisition unit configured to acquire force information relating to force acting on the endoscope insertion section; and a stress estimation unit configured to calculate information of stress relating to a stress estimation area, based on the force information.

A stress estimation method includes: acquiring force information relating to force acting on a flexible member to apply force to an inner surface of an examined body; and calculating information of stress relating to a stress estimation area, based on the force information.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view schematically showing an example of a main configuration of a sense-of-force evaluation system according to a first embodiment.

FIG. 13B showing an example of a distribution of stress in the area where stress concentrates in the intestinal tract.

FIG. 21 is a view schematically showing another example of the main configuration of the sense-of-force evaluation system according to the first embodiment.

FIG. 23 is a view schematically showing an example of a main configuration of a sense-of-force evaluation system according to a modification of the first embodiment.

FIG. 24 is a view schematically showing another example of a main configuration of a sense-of-force evaluation system according to a modification of the first embodiment.

FIG. 26 is a view schematically showing an example of a main configuration of the sense-of-force evaluation system according to the second embodiment.

DETAILED DESCRIPTION OF THE INVENTION

Figure 2:
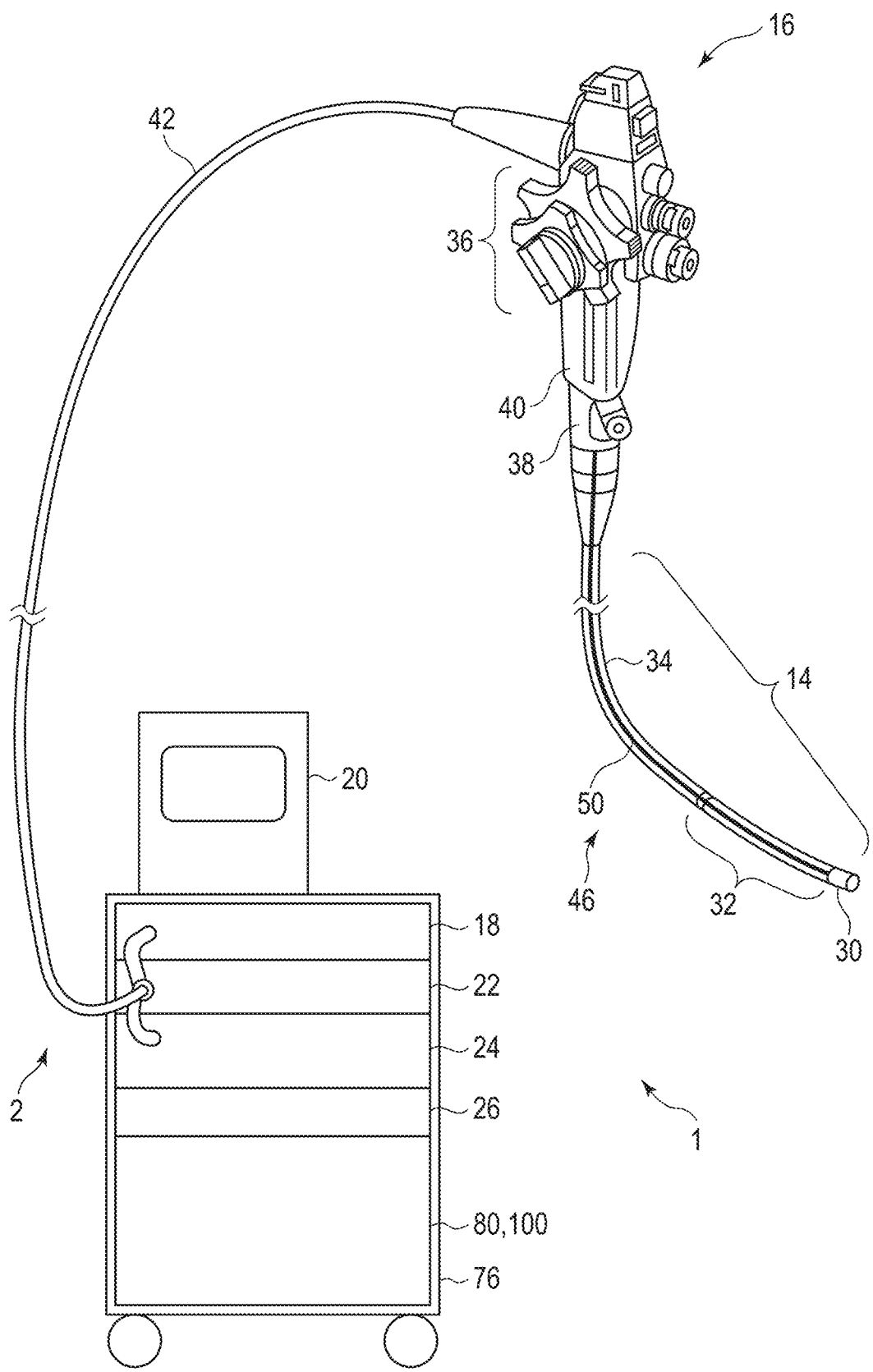
FIG. 2 is a view showing an example of a configuration of an endoscope system.

Hereinafter, a sense-of-force evaluation system according to each embodiment of the present invention will be described. The sense-of-force evaluation system is generally applied to an insertion apparatus including a flexible member, such as a medical endoscope. The sense-of-force evaluation system is also applicable to a catheter, a medical manipulator, and the like, in addition to medical endoscopes such as an upper gastrointestinal endoscope, a colonoscope, an ultrasonic endoscope, a cystoscope, and a pyeloscope.

When an operator performs works such as observation, diagnosis, therapy, and treatment, by inserting a flexible member into an examined body, force or stress occurs in the examined body, e.g. a lumen cavity, by the flexible member coming in contact with the examined body and applying force to the examined body. Here, the stress means a force acting per unit area. When force is applied from the flexible member to the examined body, various forces or stresses occur in the examined body due to an internal structure thereof, or the like. The sense-of-force evaluation system estimates such forces or stresses occurring in the examined body. Note that the resultant force of forces occurring in the examined body is balanced with the force applied from the flexible member to the examined body. In other words, the resultant force is a reaction force of the force applied to the examined body.

First Embodiment

FIG. 1 is a view schematically showing an example of a main configuration of a sense-of-force evaluation system 1, i.e. a stress estimation system, according to a first embodiment. The sense-of-force evaluation system 1 is a stress estimation system that can estimate stress occurring in an examined body 200 by a flexible member 12 that is to be inserted into an inside of the examined body 200 and to apply force to an inner surface of the examined body 200. In the sense-of-force evaluation system 1 according to the first embodiment, it is assumed that the flexible member 12 is inserted in a lumen cavity of the examined body 200, and works such as diagnosis and therapy are performed.

The sense-of-force evaluation system 1 in the present embodiment calculates shape and disposition information including shape information of the flexible member 12, which operates on the examined body 200, and disposition information relative to the examined body 200. The operation on the examined body 200 is, for example, insertion in the examined body 200, surface scan, observation, repair, diagnosis, therapy, etc. The sense-of-force evaluation system 1 calculates, based on the shape and disposition information, first sense-of-force information relating to force acting on the flexible member 12, i.e. force information. The sense-of-force evaluation system 1 calculates second sense-of-force information relating to force or stress occurring in the examined body 200, based on the shape and disposition information, the first sense-of-force information, and examined body information relating to the examined body 200. Here, the sense-of-force information is information including at least one of a position, a direction, and a magnitude of force. The second sense-of-force information is information relating to force occurring in an inside or on a surface of the examined body 200, i.e. force or stress occurring in an inside or on a surface of the examined body 200.

In particular, the sense-of-force evaluation system 1 in the present embodiment acquires, as a stress estimation system, force information relating to force acting on the flexible member 12, acquires examined body information including a length of an outer periphery of a predetermined stress estimation area in the examined body 200, which is a target area of estimation of stress, and a thickness of the examined body 200 in the stress estimation area, calculates the magnitude and direction of force applied to the examined body 200 in the stress estimation area, based on the force information, and calculates information of stress on the outer periphery of the stress estimation area, based on the calculated magnitude and direction of force, the length of the outer periphery of the stress estimation area, and the thickness of the examined body 200.

The sense-of-force evaluation system 1 shown in FIG. 1 includes an endoscope system 2 and a control apparatus 100. The endoscope system 2 includes an endoscope 10. The endoscope 10 includes an insertion section 14 as the flexible member 12. The insertion section 14 is inserted into a lumen cavity of the examined body 200.

(Examined Body and Lumen Cavity)

In the present embodiment, it is assumed that the examined body 200 is mainly a patient who undergoes diagnosis or therapeutical treatment, or an organ of the patient. Note that the examined body 200 may be a patient model or organ model for simulation, in place of the patient or organ. Alternatively, the examined body 200 may be an animal such as a mammal, a reptile, a bird, or the like. Aside from the medical field, the examined body 200 may be a device, a work, or the like, which has a tubular cavity or a space in the inside thereof.

The lumen cavity of the examined body 200, which is a target of the sense-of-force evaluation system 1 according to the embodiment, is mainly a digestive organ, a bronchus, a urinary organ, or the like. Aside from the lumen cavity, an organ, which is opened up by a surgical operation, may be the target. In the description below, the large intestine is taken as an example of the lumen cavity of the examined body 200. The large intestine has a shape and a disposition that vary from person to person, and the large intestine is an organ whose shape may particularly vary with the passing of time, or by the insertion of a device, or the like. For example, the large intestine includes a movable intestinal tract and a fixed intestinal tract. The rectum, descending colon, and ascending colon are movable intestinal tracts, which are freely movable, and the sigmoid column, transverse colon, and cecum are fixed intestinal tracts.

(Endoscope System)

Referring to FIG. 2, the endoscope system 2 will be described.

The endoscope system 2 includes the endoscope 10, an image processing device 18, i.e. a video processor, a display 20, a light source device 22, a light emission/detection device 24, and an endoscope control device 26. As described above, the endoscope 10 includes the insertion section 14 as the flexible member 12. The endoscope 10 images an observation target by an imaging element (not shown) built in the insertion section 14. The observation target may be an affected part, a lesion part, or the like in the examined body 200. The image processing device 18 image-processes an electric signal to which light from the observation target is converted by the imaging element of the endoscope 10. The display 20 displays an observation image that is image-processed by the image processing device 18. The light source device 22 emits illumination light, and supplies the illumination light to a light guide (not shown) of the endoscope 10. The light emission/detection device 24 emits light for detection, which is different from the illumination light, the light for detection being light for detection for a sensor 46 (to be described later), which is a shape sensor 50 that is a fiber sensor in this example, and the light emission/detection device 24 detects light traveling through the sensor 46. The endoscope control device 26 controls the operation of the entirety of the endoscope system 2. The devices 18, 20, 22, 24, and 26 may be accommodated in a rack 76.

The endoscope 10 includes an elongated insertion section 14 serving as the flexible member 12, and an operation unit 16. coupled to a proximal portion of the insertion section 14. The insertion section 14 includes a distal rigid section 30, a bendable section 32, and a flexible tube section 34 in the order form the distal end to the proximal end of the insertion section 14. A proximal portion of the distal rigid section 30 is coupled to a distal portion of the bendable section 32. A proximal portion of the bendable section 32 is coupled to a proximal portion of the flexible tube section 34.

The distal rigid section 30 is a distal portion of the insertion section 14, and is a distal portion of the endoscope 10. The distal rigid section 30 is rigid, and an imaging element, an illumination optical system, an observation optical system, and the like are built in the distal rigid section 30. Illumination light from the illumination device 22 is radiated on the observation target from the illumination optical system at the distal end face of the distal rigid section 30 through the light guide.

The bendable section 32 is configured such that node rings (not shown) are coupled along the longitudinal axis direction of the insertion section 14. The bendable section 32 bends in a desired direction in accordance with an operation that is input to a bend operation section 36 provided in the operation unit 16. For example, a worker such as a doctor, who is an operator, operates the operation unit 16, and thereby the bendable section 32 is bent and the position and direction of the distal rigid section 30 are changed. Thereby, the endoscope 10 captures the observation target within the observation view field.

The flexible tube section 34 has a desired flexibility, and is bent by an external force. The flexible tube section 34 is a tubular member extending from a main body section 38 of the operation unit 16.

In the endoscope 10, the operator can insert the insertion section 14 into a lumen cavity such as a digestive organ, a bronchus, a urinary organ, or the like of the patient that is the examined body, while bend-operating the bendable section 32 or turning the flexible tube section 34.

Note that although the insertion section 14 includes the distal rigid section 30 and bendable section 32, the distal rigid section 30 is a very short portion and the bendable section 32 is configured to be bendable, and thus the term "flexible member 12" in the present specification is used to generally mean the insertion section 14.

Figure 3:
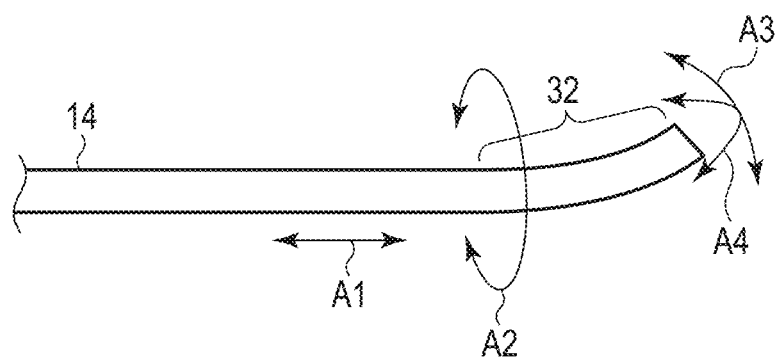
FIG. 3 is a view showing an example of an operation direction of an insertion section of an endoscope.

FIG. 3 is a view schematically showing an insertion/drawing direction, a bend direction, and a rotational direction as operation directions of the insertion section 14. The operation directions of the insertion section 14 include an insertion/drawing direction of the insertion section 14 inserted in the lumen cavity, as indicated by a double-headed arrow A1 in FIG. 3, and a turning direction, i.e. a rotational direction, of the insertion section 14, as indicated by a double-headed arrow A2. Further, the operation directions of the insertion section 14 include a vertical direction of the bendable section 32 by the operation of the bend operation section 36, as indicated by a double-headed arrow A3, and a left-and-right direction of the bendable section 32 by the operation of the bend operation section 36, as indicated by a double-headed arrow A4.

The operation unit 16 includes the main body section 38 from which the flexible tube section 34 extends, and a gripper 40 that is coupled to a proximal portion of the main body section 38. The gripper 40 is grasped by the operator who operates the endoscope 10. In the gripper 40, the bend operation section 36 is disposed. In addition, a universal cord 42 extends from the operation unit 16. The universal cord 42 includes an imaging electric cable, alight guide, and the like, which extend from the insertion section 14. The endoscope 10 is connected through the universal cord 42 to various devices such as the image processing device 18, light source device 22, light emission/detection device 24, endoscope control device 26, and control apparatus 100.

(Sensor)

Figure 4:
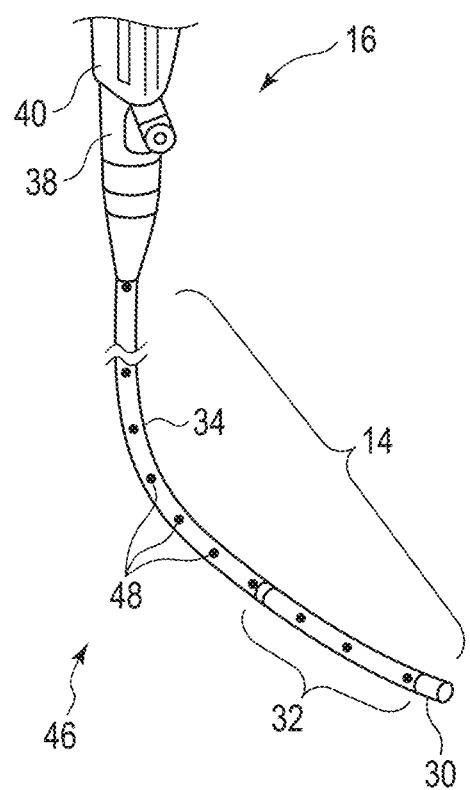
FIG. 4 is a view showing an example of a position sensor assembled in the insertion section.

The sense-of-force evaluation system 1 includes the sensor 46. The sensor 46 in the present embodiment is at least one of a position sensor 48 and the shape sensor 50. The position sensor 48 is a sensor configured to detect the position of the insertion section 14. The shape sensor 50 is a sensor configured to detect the shape of the insertion section 14. For example, FIG. shows, as the sensor 46, the shape sensor 50 that is disposed along the longitudinal direction of the insertion section 14. For example, FIG. 4 shows, as the sensor 46, position sensors 48 arranged at intervals along the longitudinal direction of the insertion section 14. For example, FIG. 5 shows the sensor 46 including the shape sensor 50 and position sensors 48.

The sensor 46, together with a shape and disposition information calculator 102 (to be described later) of the control apparatus 100, constitutes a shape and disposition information detector 52.

Figure 5:
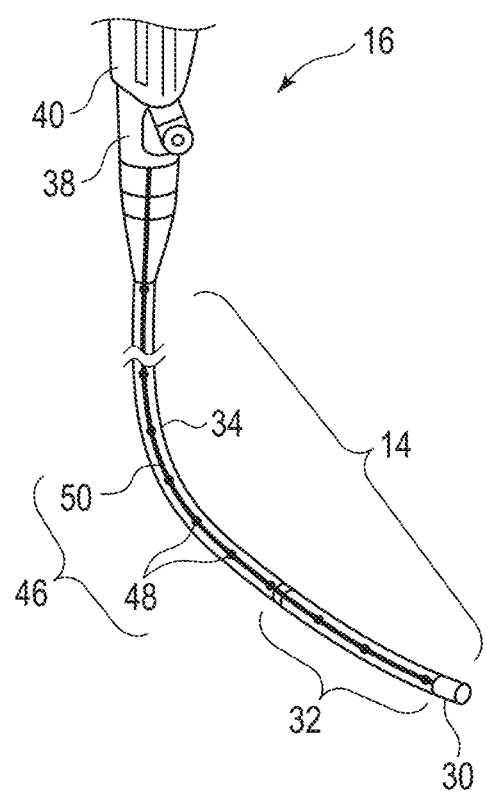
FIG. 5 is a view showing an example of a position sensor and a shape sensor assembled in the insertion section.
Figure 6:
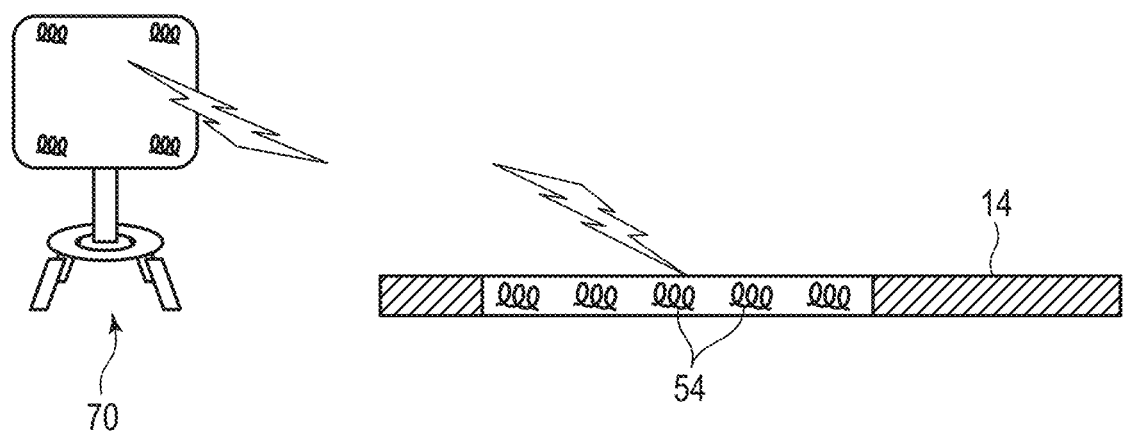
FIG. 6 is a view showing an example of a configuration of a magnetic-type position sensor.

The position sensors 48 shown in FIG. 4 and FIG. 5 are, for example, of a magnetic type. In this type of position sensors 48, as shown in FIG. 6, magnetic coils 54 are provided in the insertion section 14. In addition, a magnetic antenna 70 serving as a receiver is fixed and installed in a room. The magnetic coils 54 generate a magnetic field by receiving an electric current as a magnetic field generating signal that is output from a signal generator (not shown). The magnetic antenna 70 detects a generated magnetic field. Based on the detected magnetic field, the shape and disposition information calculator 102 calculates the position of the insertion section 14 in which the magnetic coils 54 are disposed. Note that if the magnetic antenna 70 is attached to the examined body 200, the relative position of the insertion section 14 to the examined body 200 can be detected. The transmission/reception relation may be reversed by using the magnetic antenna 70 as a transmission antenna and by providing reception coils in the insertion section 14.

In addition, the shape and disposition information detector 52 including the magnetic-type position sensors 48 can also detect the direction. By arranging magnetic coils 54 at different positions in a circumferential direction at an identical position in the longitudinal direction of the insertion section 14, the shape and disposition information detector 52 can detect not only the position but also the disposition and attitude of the insertion section 14.

The method of the position sensors 48 is not limited to the magnetic method, but may be an ultrasonic method, an optical method, a method using an acceleration sensor, or the like. It suffices that the shape and disposition information detector 52 including the position sensors 48 can detect the position or the relative position of the insertion section 14 to the examined body 200 or a place, such as a room, where the examined body 200 is placed. In addition, an insertion section sensor configured to detect an insertion amount and a rotation amount of the insertion section 14 may be used as the position sensor for detecting the relative position of the insertion section 14 to the examined body 200. For example, the relative position of the insertion section 14 to the examined body 200 can be detected by combining the insertion section sensor disposed at an inlet of the examined body 200 and the position sensors 48.

For example, as shown in FIG. 4 and FIG. 5, in the shape and disposition information detector 52 including the position sensors 48, when the position sensors 48 are arranged at intervals along the longitudinal direction of the insertion section 14, the shape of the insertion section 14 can be detected by interpolating the detection positions.

The shape sensor 50 shown in FIG. 2 and FIG. 5 is, for example, a fiber sensor configured to detect a bend shape from a curvature of a specific part by using an optical fiber. The fiber sensor is suitable as the shape sensors 50, because the fiber sensor has a small diameter and is easily assembled in the insertion section 14, and the fiber sensor is hardly affected by other structures. The shape sensor 50 that is the fiber sensor includes, for example, an optical fiber that is disposed along the longitudinal direction of the insertion section 14. The optical fiber is provided with sensing parts arranged at intervals along the longitudinal direction. In the fiber sensor, light for detection is supplied to the optical fiber from the above-described light emission/detection device 24. The shape and disposition information calculator 102 calculates the shape of the insertion section 14, based on a variation amount of light at each sensing part at a time when the supplied light travels through the optical fiber. Note that the shape and disposition information calculator 102 may be included in the light emission/detection device 24.

The shape sensor 50 is not limited to the fiber sensor, but may be any kind of sensor if the sensor satisfies conditions of the function, size, etc. For example, the shape of the insertion section 14 may be calculated from one or more camera images.

In this manner, the shape and disposition information detector 52 including the sensor 46 and the shape and disposition information calculator 102 is not particularly limited with respect to a concrete detection method, an assembly method, etc., if the shape and disposition information detector 52 has specifications of sufficient capability in function, a size, etc.

(Control Apparatus)

The control apparatus 100 includes the above-described shape and disposition information calculator 102, a first sense-of-force information calculator 104, a second sense-of-force information calculator 108, an examined body information estimation unit 110, a contact state estimation unit 112, an examined body influence judgment unit 114, and an information output unit 116. Each calculator or each unit is composed of a processor including an integrated circuit or integrated circuits, such as a CPU. For example, a software program for causing the processor to function as these parts is prepared in a memory (not shown), and the processor executes this program, and thereby the processor may perform the functions of the respective parts. The control apparatus 100 also includes a mechanical characteristic storage unit 106 and an output information storage unit 118. The storage units 106 and 118 are storages such as nonvolatile semiconductor memories.

The above-described parts of the control apparatus 100 are accommodated, for example, in a housing 80 shown in FIG. 2. The control apparatus 100, like the other devices 18, 20, 22, 24, and 26, may be mounted in the rack 76.

The respective parts of the control apparatus 100 may be included in a control apparatus that is different from the control apparatus 100. For example, the respective parts may be included in the image processing device 18 or the endoscope control device 26. Alternatively, each of the respective parts may be included in a control apparatus that is different from the image processing device 18 or the endoscope control device 26. Specifically, a hardware circuit, such as a processor or an FPGA, which functions as each part of the control apparatus 100, may be included in a housing or in housings, as far as the function of each part can be implemented. For example, each of the respective parts may be disposed in the insertion section 14 or may be placed in a remote place connected by communication. Each storage unit 106, 118 may similarly be a storage unit or storage units, or may be an external storage device that is separate from the control apparatus 100 and is connected by communication.

(Shape and Disposition Information Calculator)

The shape and disposition information calculator 102 calculates, as described above, shape and disposition information including the shape information of the insertion section 14 and the disposition information relative to the examined body 200, based on the detection result by the sensor 46. When the information directly obtained from the sensor 46 is not in the form of coordinates or in the form of a shape, the shape and disposition information calculator 102 executes a process of processing the obtained information into a desired form. It is preferable that the shape information includes a curvature, and that the disposition information is based on coordinates of an inertial coordinate system. However, any kind of expression method may be adopted if the sense-of-force information relating to the force or stress occurring in the examined body 200 can finally be obtained.

Even if the shape and disposition information of the entirety of the insertion section 14 is not directly found from the information obtained from the sensor 46, the shape and disposition information calculator 102 calculates, as needed, the information necessary for calculating the sense-of-force information relating to the force or stress occurring in the examined body 200, for example, by interpolating the position or shape of the insertion section 14 with respect to the information of position or the information of shape detected by the sensor 46. Specifically, the shape and disposition information calculator 102 virtually segments the insertion section 14 and calculates the position, direction, bend amount, etc. of each segment, in order to use them in the calculation or the like of first sense-of-force information and second sense-of-force information to be described later.

The shape and disposition information calculated by the shape and disposition information calculator 102 is output to the first sense-of-force information calculator 104 and second sense-of-force information calculator 108.

(Mechanical Characteristic Storage Unit)

The mechanical characteristic storage unit 106 stores mechanical characteristic information representing the mechanical characteristics of the insertion section 14. The mechanical characteristic storage unit 106 stores, for example, values relating to the mechanical characteristics of each of the segments into which the insertion section 14 is segmented. In other words, the mechanical characteristic storage unit 106 stores mechanical characteristic information representing the mechanical characteristics at positions in the longitudinal direction of the flexible member 12. The mechanical characteristics are indices indicative of the mechanical characteristics of each segment of the insertion section 14. Examples of the mechanical characteristics include a Young's modulus of each segment, a mass, a magnitude of a torsional moment necessary for causing a certain torsion amount, a magnitude of compressive force/ tensile force necessary for a certain extension/contraction, and a flexural rigidity. The flexural rigidity is an index indicative of the difficulty in bending of each segment of the insertion section 14. If the first sense-of-force information can be obtained by executing a process to be described, the mechanical characteristic may be replaced with some other quantitative expression.

Although depending on the detection precision of a sense-of-force, it is not always necessary to strictly store the mechanical characteristics of each segment. The values of certain mechanical characteristics of the entirety of the insertion section 14 may be represented by one value, or a less number of values than the number of segments may be used. In addition, the values of mechanical characteristic may not be values for each segment, but may be an arrangement of values, a function, or the like, which corresponds to the distance from the distal end to proximal end of the insertion section 14. In addition, the values of mechanical characteristics may be stored as constants in the first sense-of-force information calculator 104, for example, as a part of a program, or may be stored together in the first sense-of-force information calculator 104.

For example, if the values of mechanical characteristics can be set for each of individual insertion sections 14, the detection precision of a sense-of-force can be enhanced. In addition, if the values of mechanical characteristics are made changeable, the latest values corresponding to a change with time of the insertion section 14 can be used in the first sense-of-force information calculator 104.

(First Sense-of-force Information Calculator)

The first sense-of-force information calculator 104 acquires the shape and disposition information of the insertion section 14 from the shape and disposition information calculator 102. The first sense-of-force information calculator 104 acquires the mechanical characteristic information of the insertion section 14 from the mechanical characteristic storage unit 106. Based on the shape and disposition information and the mechanical characteristic information, the first sense-of-force information calculator 104 calculates first sense-of-force information that is sense-of-force information relating to force acting at one or more positions in the longitudinal direction of the insertion section 14. Note that, as regards the information used in the calculation of the first sense-of-force information, the shape and disposition information of the insertion section 14 is not limited to the shape and disposition information of the insertion section 14 that is acquired from the shape and disposition information calculator 102. The first sense-of-force information calculator 104 may calculate the first sense-of-force information by using some other sensor or calculator that can acquire the force acting on the insertion section 14.

As described above, the sense-of-force information is information of force, which includes at least one of the position at which force acts, the direction of force, and the magnitude of force. The position, direction, or magnitude, which is already known, may be excluded from the first sense-of-force information that is calculated here. In addition, unnecessary information, for example, information that is not presentation information to the operator and the like, may also be excluded.

The calculation of the first sense-of-force information is performed, for example, based on a mechanical principle. Examples of the calculation of the first sense-of-force information are shown below.

(Detection principle 1) In each segment, "a first internal force Fs estimated from a deformation state" and "a second internal force Ff estimated from force applied from an outside" are substantially equal.

(Detection principle 2) In each segment, "a first bending moment Mb estimated from shape information" and "a second bending moment Mf estimated from force applied from an outside" are substantially equal.

These are based on a static balance, and it is presupposed that the movement of the insertion section 14 and examined body 200 is slow. In the insertion, diagnosis, and medical treatment by the insertion apparatus such as the endoscope 10, since the insertion section 14 and examined body 200 move generally slowly, the presupposition is applicable. Therefore, a result with high precision is assumed.

In the calculation of the first sense-of-force information, a mechanical principle other than the static balance, for example, a dynamical equation of motion, may be used, or a combination of the static balance and some other mechanical principle may be used. In addition, an equation, in which the manner of physical expression is changed, may be used.

Hereinafter, the outline of calculation of the first sense-of-force information with respect to the detection principle 2, which is a concrete example of the detection principle 1, will be described.

Figure 7:
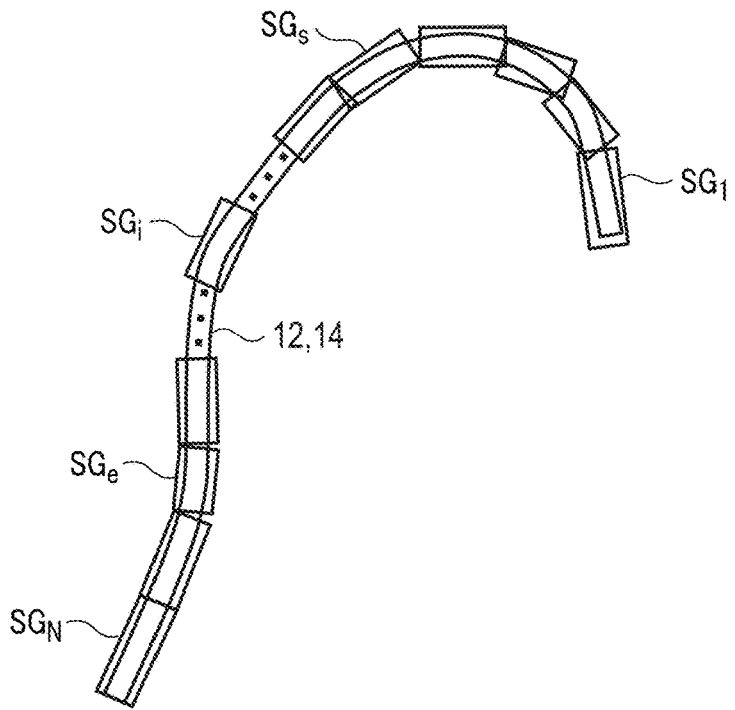
FIG. 7 is a view for describing a concept of segmentation of the insertion section.

FIG. 7 shows a state of segmentation of the insertion section 14 of the endoscope 10. In FIG. 7, it is assumed that there are an N-number of segments from a distal segment 1 to a proximal segment N of the insertion section 14. Among these segments, $N_s$ segments from a segment $SG_s$ to a segment $SG_e$ are calculation targets.

In the calculation of the first sense-of-force information that is based on the static balance, the first sense-of-force information calculator 104 calculates, with respect to each segment, a first bending moment $M_b$ estimated from shape information, and a second bending moment $M_f$ estimated from force applied from the outside. Thereby, conditional expressions, in which the first bending moment $M_b$ and the second bending moment $M_f$ are substantially equal, can be formed, the number of conditional expressions being equal to the number $N_s$ of the segments of the insertion section 14, for which the calculations are performed.

On the other hand, in the first sense-of-force information calculated, there are variables, the number of which is equal to a product between a number $N_f$ of forces and of a number $N_c$ of information contents to be calculated, i.e. there are $N_f \times N_c$ variables.

When an equation below is established, the values of variables can uniquely be calculated.

Number ($N_s$) of conditional expressions=Number ($N_f \times N_c$) of variables In addition, when an expression below is established, the values of variables cannot uniquely be calculated, and a combination of solutions of variables, which are considered to be appropriate, is calculated. Normally, the combination of solutions is calculated by an optimization method in which a specific evaluation expression is set to a minimum or a maximum.

Number ($N_s$) of conditional expressions>Number ($N_f \times N_c$) of variables The first sense-of-force information calculator 104 calculates, i.e. estimates, the first bending moment $M_b$, from the mechanical characteristic information, e.g. a flexural rigidity value, and the shape information in each segment of the insertion section 14. The mechanical characteristic information is acquired from the mechanical characteristic storage unit 106. The shape information is acquired from the shape and disposition information calculator 102.

For the purpose of simplification, a calculation method in the case of two dimensions will be described.

It is assumed that each segment is straight when no bending moment is applied. However, the part of the bendable section 32 is bendable by a bending operation, and, in some cases, the shape thereof is not straight when a bending moment by external force is not applied. Accordingly, as regards this part, a state in which no external force is applied is set as a reference, and the first bending moment $M_b$ is calculated based on a change from this state. Note that, for the purpose of simplification, the bendable section 32 may be excluded from the segments of the calculation targets.

Figure 8:
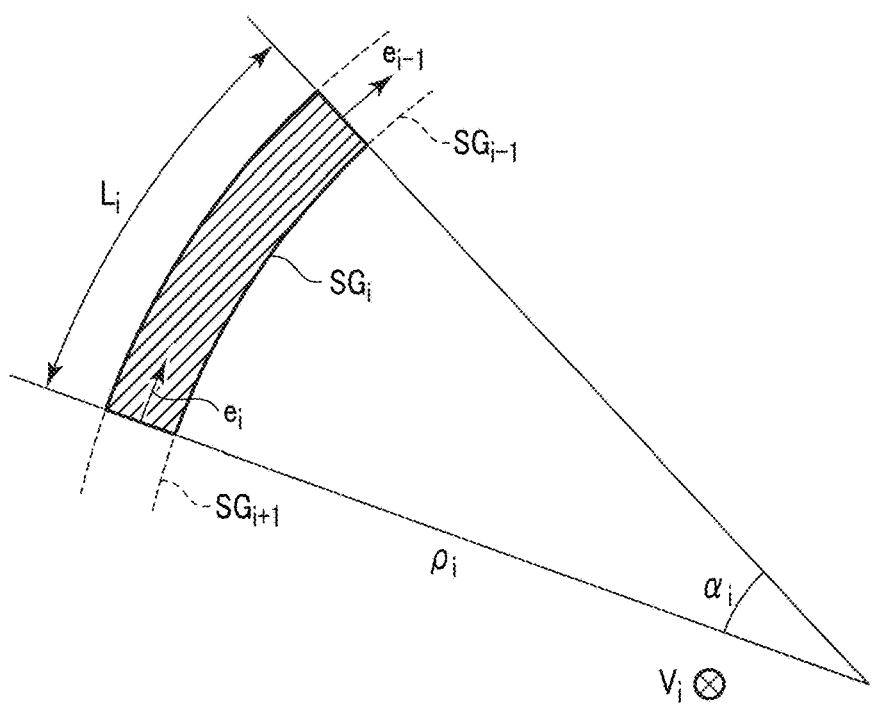
FIG. 8 is a view showing an example of a bend shape of one segment.

FIG. 8 shows a bend shape of a segment $SG_i$ that is an i-th segment. Here, the shape of the segment $SG_i$ is approximated to an arc.

Here, definitions are given as below. Note that, hereinafter, "i" is a subscript corresponding to the segment $SG_i$.

Bending moment estimated from shape: $Mb_i$,
Young's modulus: $E_i$,
Second moment of area: $I_i$,
Direction vector of segment $SG_i$: $e_i$, where the direction vector $e_i$ is a direction vector at a connection portion between a segment $SG_{i+1}$ and a segment $SG_i$, and is directed toward the segment $SG_{i-1}$.
Direction vector perpendicular to the drawing sheet: $V_i$,
Curvature: $\chi_i$ (=$1/p_i$),
where $p_i$ is a radius of curvature.
Flexural rigidity: $G_i$ (=$E_i \cdot I_i$).

At this time, with respect to an arbitrary segment $SG_i$, the following relationships are established from mechanics of materials.

$$Mb_i = E_i / p_i \cdot I_i \qquad \text{equation 1}$$

$$\alpha_i = L_i / p_i \qquad \text{equation 2}$$

where $\alpha_i$ [rad].

From equations 1 and 2, the following relationship is derived.

$$Mb_i = (\alpha_i / L_i) \cdot (E_i \cdot I_i) = \chi_i \cdot G_i \qquad \text{equation 3}$$

Here, "$E_i \cdot I_i = G_i$" is called flexural rigidity.

From equation 3, the first bending moment Mb in the segment $SG_i$, which is estimated from the bend shape or the shape information, is calculated.

$G_i$ may be slightly variable in accordance with the magnitude of the curvature $\chi_i$. Thus, $G_i$ may be treated by being regarded as a constant, or, if exactness is required, $G_i$ may be treated by being regarded as a variable of the curvature $\chi_i$.

In the two dimensions, when the segment $SG_{i-1}$ side, which is closer to the distal end of the insertion section 14, bends to the left, the bending moment $Mb_i > 0$, and the angle $\alpha_i > 0$.

In addition, the first sense-of-force information calculator 104 calculates or estimates the second bending moment $M_f$ by force applied from the outside, the second bending moment $M_f$ occurring in each segment of the insertion section 14.

Figure 9:
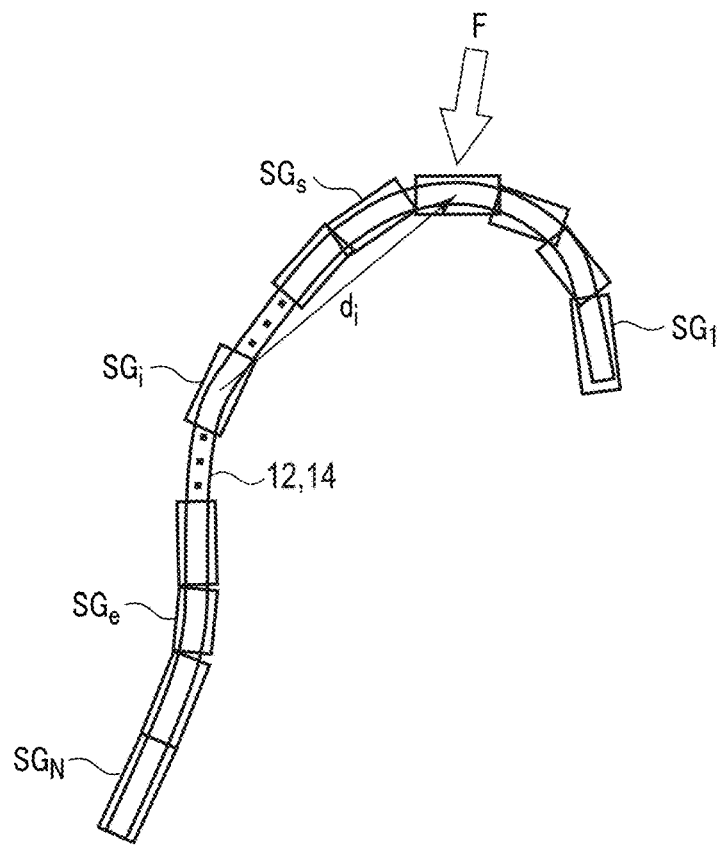
FIG. 9 is a view showing a pushing force F that is applied to the insertion section from an examined body, and a vector $d_i$ from the center of a segment $SG_i$ to a position at which the pushing force F is applied.

As regards concrete calculations, for the purpose of simplification, a description will first be given of a case in which one force acts on the insertion section 14. In FIG. 9, the second bending moment $Mf_i$, which is applied to the segment $SG_i$ by external force, is mechanically shown as below.

<<Case of Two Dimensions (XY Coordinates)>>

When a position where a pushing force F that is a vector is applied is located on the distal side of the position of the segment $SG_i$, the second bending moment $Mf_i$ is as follows. Note that the second bending moment $Mf_i$ is a scaler, and has a value (+) at a time of a counterclockwise bending moment.

$$Mf_i = z \text{ component of } (d_i \times F) \qquad \text{equation 4a}$$

where "x": an outer product, $d_i$: a vector from the center of the segment $SG_i$ to a position where the pushing force F is applied.

The following may also be possible:

$$Mf_i = |d_i \times F| \text{ (absolute value)}$$

In addition, when the position where the pushing force F is applied is located on the proximal side of the position of the segment $SG_i$, the second bending moment $Mf_i$ is as follows.

$$Mf_i = 0 \qquad \text{equation 4b}$$

This is a scalar.

<<Case of Three Dimensions>>

When a position where a pushing force F that is a vector is applied is located on the distal side of the position of the segment $SG_i$, the second bending moment $Mf_i$ is as follows. Note that the second bending moment $Mf_i$ is a vector.

$$Mf_i = d_i \times F \qquad \text{equation 4c}$$

In addition, when the position where the pushing force F is applied is located on the proximal side of the position of the segment $SG_i$, the second bending moment $Mf_i$ is as follows.

$$Mf_i = 0 \qquad \text{equation 4d}$$

This is a 0 vector. The 0 vector is a vector with a magnitude of 0.

When a plurality of forces act, a resultant force of the forces may be calculated for a pushing force $F_j$ with respect to which the position where the force is applied is located on the distal side of the position of the segment $SG_i$. When the force is a distributed load, the force may be regarded as concentrating on a plurality of specific points, as will be described later.

<<Case of Two Dimensions (XY Coordinates)>>

In this case, the second bending moment $Mf_i$ is as follows.

$$Mf_i = z \text{ component of } [\Sigma(d_{ij} \times F_j)] \qquad \text{equation 5a}$$

where only the force on the distal side of the position of the segment $SG_i$ is calculated.

Here, $F_j$: external force (vector), and

"x": an outer product.

The following may also be possible:

$$Mf_i = |\Sigma d_{ij} \times F_j| \text{ (absolute value)}$$

<<Case of Three Dimensions>>

In this case, the second bending moment $Mf_i$ is as follows.

$$Mf_i = \Sigma(d_{ij} \times F_j) \qquad \text{equation 5b}$$

where only the force on the distal side of the position of the segment $SG_i$ is calculated.

The first sense-of-force information calculator 104 calculates, as the first sense-of-force information, at least a necessary one of the position, direction, and magnitude of force, based on a relationship, Mfi≈Mbi between the first bending moment Mbi and the second bending moment Mfi. For example, at least one of the position where the pushing force F or $F_j$ is applied, the direction of the pushing force F or $F_j$, and the magnitude of the pushing force F or $F_j$.

Using the above method, the first sense-of-force information calculator 104 calculates the first sense-of-force information relating to the force acting on the insertion section 14, which is the flexible member 12. The first sense-of-force information is output to the second sense-of-force information calculator 108.

(Examined Body Information Estimation Unit)

The examined body information estimation unit 110 estimates examined body information. The examined body information includes the shape and disposition of the examined body 200, the anatomical disposition, the tensile strength, and the area or position of a fixing part. Here, the fixing part is a part at which the examined body 200 is fixed to a structure on the outside of the examined body 200.

The examined body information may be information of the examined body 200 acquired in real time during the insertion of the endoscope, information measured in advance with respect to the examined body 200 by other equipment such as a CT (Computed Tomography), measurement information at a time when the endoscope was previously inserted into the examined body 200, or information used previously. However, the examined body information cannot always be acquired in advance or in real time. Thus, preset values may be used as general values for the information such as the shape and disposition of the lumen cavity of the examined body 200, the tensile strength, the fixed position, and the like, or values may be used that are preset in accordance with the physical features such as the body height, body weight, abdominal circumference, age, gender, etc. Specifically, the examined body information may be estimation information that is estimated from input information including personal data of the examined body 200, or may be general human body model information. In addition, it is also effective to update, where necessary, the examined body information while the endoscope is being inserted into the examined body 200. When the examined body 200 is a device, a structure, or the like other than the human body and animal, the examined body information is information of the structural disposition, etc. of the device, structure, or the like.

For example, the shape and disposition of the intestinal tract, which is the lumen cavity of the examined body 200, and the information of the fixed position, are estimated or measured from the shape and disposition of the insertion section 14, which is the flexible member 12, and thereby the direction and magnitude of the force acting on the intestinal tract can be estimated.

In that part of the intestinal tract in which the insertion section 14 is inserted, the shape and disposition information of the intestinal tract in that part can be acquired by obtaining the shape and disposition information of the insertion section 14. In addition, as regards that part of the intestinal tract, which is located on the distal side with respect to the distal end of the insertion section 14, the estimation can be performed to some extent from the shape and disposition information of the vicinity of the distal end of the insertion section 14. At this time, the information relating to the disposition of the intestinal tract may be obtained, as needed, to improve the precision of the estimation. For example, if there is a history of previous endoscope insertion, there is a possibility that the shape and disposition of the intestinal tract, and the fixed position, can be estimated from the insertion path based on the history. It is assumed that the information of the fixing part of the intestinal tract is given by estimation, measurement, or the like. The same applies to the thickness of the intestinal tract.

(Second Sense-of-force Information Calculator)

The second sense-of-force information calculator 108 acquires the first sense-of-force information relating to the force acting on the insertion section 14 from the first sense-of-force information calculator 104. Specifically, the second sense-of-force information calculator 108 acquires, as a force information acquisition unit, force information relating to the force acting on the flexible member 12. The second sense-of-force information calculator 108 acquires, as an examined body information acquisition unit, the examined body information from the examined body information estimation unit 110. The second sense-of-force information calculator 108 acquires, from the contact state estimation unit 112, contact state information between the insertion section 14 and the examined body 200. Based on the acquired information, the second sense-of-force information calculator 108 calculates the second sense-of-force information relating to the force or stress occurring in the lumen cavity of the examined body 200. For example, the second sense-of-force information calculator calculates, as a stress estimation unit, the stress occurring in the examined body 200.

When the second sense-of-force information is calculated, the examined body information, in particular, is necessary. The reason for this is that the force occurring in the examined body 200 varies depending on the shape and disposition of the lumen cavity of the examined body, the fixed position, etc. In addition, when damage to the examined body 200 is considered, the information of the tensile strength or the like of the lumen cavity of the examined body 200 is also important.

There are two cases in which the insertion section 14 in the lumen cavity of the examined body 200 applies force to the examined body 200. In one case, the insertion section 14 pushes, mainly, an organ through the lumen cavity. In the other case, the insertion section 14 pushes, mainly, the intestinal tract, and, for example, pulls an area around the part on which the insertion section 14 is pushed.

Figure 10:
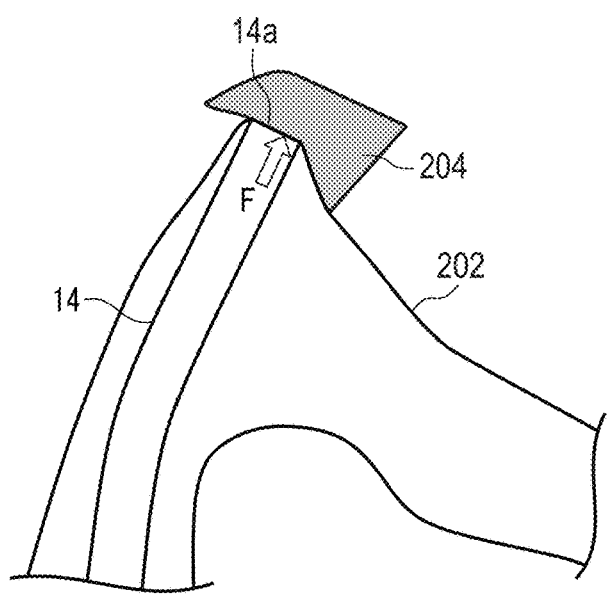
FIG. 10 is a view showing an example of a state in which the insertion section pushes up an intestinal tract and an organ.
Figure 11:
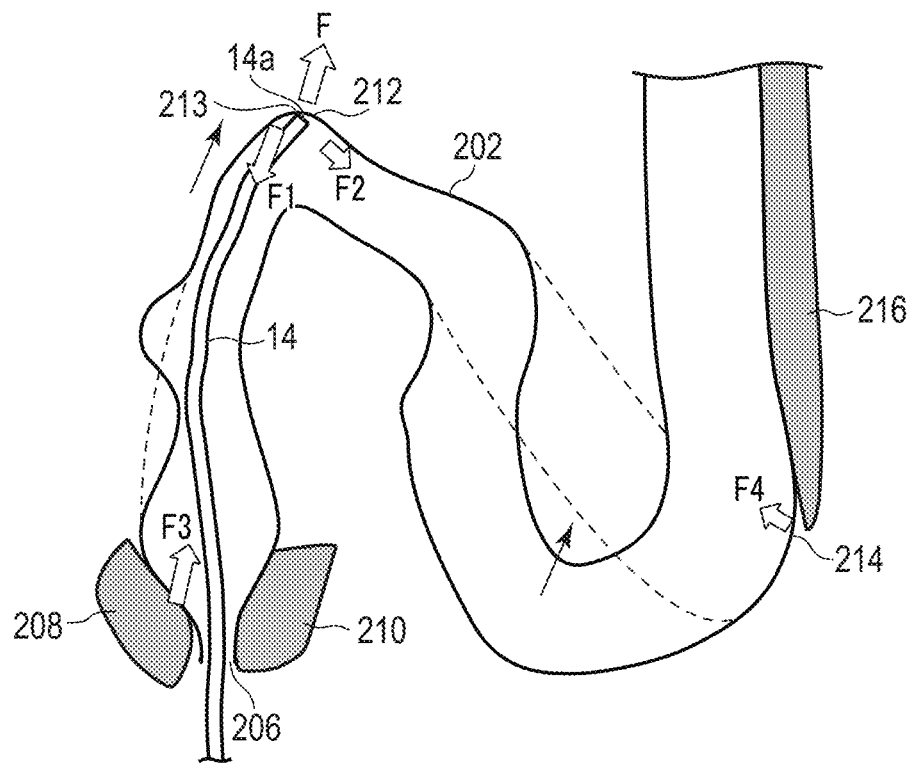
FIG. 11 is a view showing an example of force occurring in the examined body when the insertion section pushes up the intestinal tract.

FIG. 10 shows the state in which an insertion section distal end 14a pushes, mainly, an organ 204 through an intestinal tract 202. The organ 204 is, for example, the diaphragm. FIG. 11 shows a force F with which the insertion section distal end 14a pushes the intestinal tract 202 in the vicinity of the S-top 212, which is one of bend portions of the sigmoid colon, and forces F1 and F2 with which the intestinal tract 202 is pulled when the insertion section distal end 14a pushes the intestinal tract 202.

If the intestinal tract 202 is in a slack state, there occurs little force to pull the intestinal tract 202. Specifically, the force influencing the examined body 200 in such a state is the force acting on the intestinal tract 202 or acting on the organ 204 through the intestinal tract 202. There is a possibility that this force is a cause of a pain of the patient.

As regards the case in which the insertion section 14 pushes the organ 204 through the lumen cavity, if a range with a cross-sectional area S is pushed by force F, a pressure p that is generated is expressed as shown below.

$$p = F/S \quad \text{equation 6}$$

The pressure p occurs in the intestinal tract 202 at the contact part with the insertion section 14, or in the organ 204 through the intestinal tract 202, and may become a cause of damage, pain, or the like to the examined body 200.

For example, in FIG. 10, if the radius of the insertion section 14, which is the flexible member 12 of the endoscope 10, is r, the area S, where the insertion section distal end 14a pushes the organ 204 in the contact part, is $S = \pi r^2$. Here, the pressure p acting in the organ 204 per unit area is expressed as follows.

$$p = F/S = F/\pi r^2 \quad \text{equation 7}$$

Note that the value p of the pressure is an average value, and if a corner portion or edge portion of the insertion section distal end 14a is abutted, a pressure greater than this value may locally occur.

When a part of a predetermined length in an intermediate portion of the insertion section 14, i.e. an intermediate portion in the longitudinal direction of the insertion section 14 between the distal end and the proximal end of the insertion section 14, pushes the examined body 200, the second sense-of-force information calculator 108 acquires, from the contact state estimation unit 112, the contact state information indicative of the contact state between the intermediate portion and the examined body 200. For example, referring to the acquired contact state information, the second sense-of-force information calculator 108 calculates a contact area between the intermediate portion and the examined body 200, and calculates the pressure in the same manner as indicated by equation 7.

When the insertion section 14 of the endoscope 10 pushes the intestinal tract 202 or when the area around the abutted part is pulled, some patterns, i.e. some parts, where a particularly great influence on the examined body 200 occurs, can be considered. For example, the following:

i) A part on which the insertion section 14 is abutted, ii) A part on which force or stress concentrates in the intestinal tract, and iii) A peripheral part of an intestinal tract fixing part 208, 210, 216 (see forces F3 and F4 indicated by arrows in FIG. 11).

The parts of above (i) to (iii) are crushed, extended, or pulled, and consequently damage is caused to the examined body 200 and, for example, the patient feels a pain.

In the present embodiment, the second sense-of-force information calculator 108 calculates the second sense-of-force information relating to the force or stress in these parts. Hereinafter, the calculation of the force or stress in these parts will be described.

One of the influences by the abutment of the insertion section 14 upon the intestinal tract 202 is perforation of the intestinal tract 202. Perforation of the intestinal tract 202 may occur in the contact part of the above (i). Besides, in other parts, for example, in the part like the above (ii), the intestinal tract 202 may often be broken. In particular, in some cases, the operator may not be aware of the breakage of the part like the above (ii).

Figure 12A:
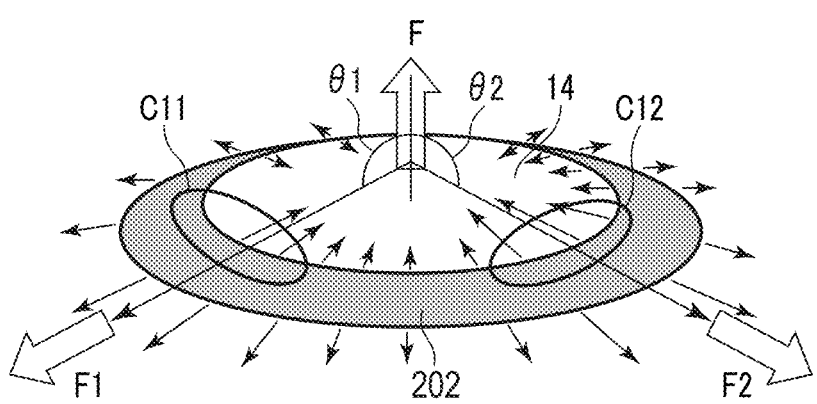
FIG. 12A is a view showing an example of force acting in a contact state in which the insertion section pushes the intestinal tract.
Figure 12B:
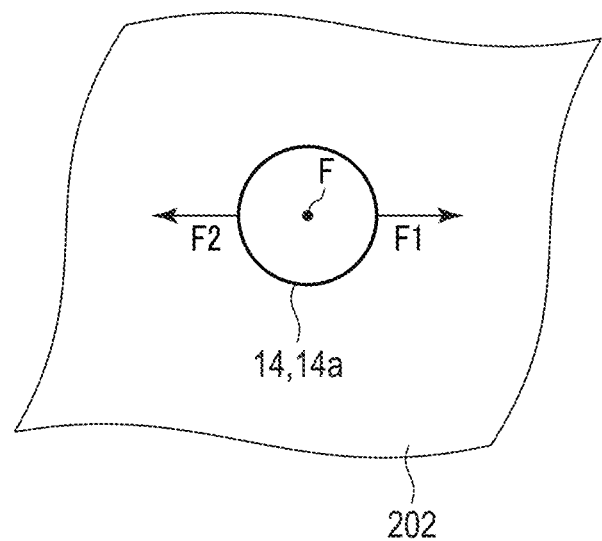
FIG. 12B is a view showing an example of a cross section in a case where the contact state in which the insertion section pushes the intestinal tract is viewed from above an insertion section distal end.
Figure 12C:
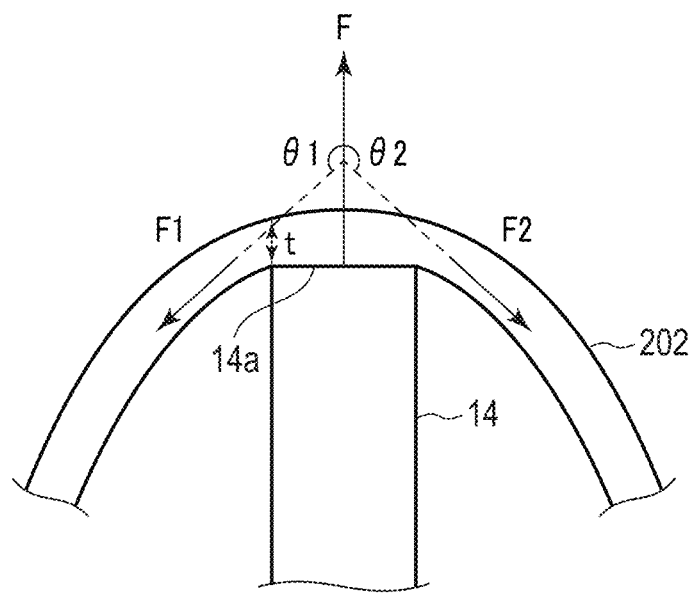
FIG. 12C is a view showing an example of a cross section in a case where the contact state in which the insertion section pushes the intestinal tract is viewed from an axial direction the insertion section.

Referring to FIG. 12A to FIG. 12C, a description will be given of a stress σ that occurs in the examined body 200 when the insertion section 14 is abutted on the intestinal tract 202, for example, when the insertion section 14 pushes, by the force F, the range of a circumferential length C, i.e. the length of the outer periphery of the part where the insertion section 14 is in contact with the intestinal tract 202 having a thickness t.

Consideration is now given to a surface where the insertion section 14 is in contact with the intestinal tract 202 and pushes the intestinal tract 202, as shown in FIG. 12A. In association with the force F with which the insertion section 14 pushes the intestinal tract 202, there occur a force F1 that pulls the intestinal tract 202 toward the anus side, and a force F2 that pulls the intestinal tract 202 toward the cecum side. Since the forces F1 and F2 are the reaction force of the external force F, the three forces F, F1, and F2 are balanced.

A simple example is assumed. When the magnitude of the force F1 and the magnitude of the force F2 are equal, an angle formed between F and F1 is θ1 and an angle formed between F and F2 is θ2, the following two equations are established in order that the three forces F, F1, and F2 are balanced.

$$F1 \cos θ1 + F2 \cos θ2 + F = 0 \quad \text{equation 8}$$

$$F1 \sin θ1 = F2 \sin θ2 \quad \text{equation 9}$$

For example, when such a degree of force acts that the intestinal tract 202 is pulled from the intestinal tract fixing parts 208, 210, and 216, the values of the angles θ1 and θ2 are estimated from the examined body information based on the structure of the inside of the examined body 200, which is acquired from the examined body information estimation unit 110, or from the contact state information acquired from the contact state estimation unit 112. From equation 8 and equation 9, the forces F1 and F2 can be expressed by using the force F and the angles θ1 and θ2.

The forces F1 and F2 shown in FIG. 12A to FIG. 12C function as the forces that pull the intestinal tract 202, and the forces F1 and F2 act on the circumferential length C of the part where the insertion section 14 is in contact with the intestinal tract 202. If average force acts on the circumferential length C, with the thickness of the intestinal tract 202 being t, a plane of a cross-sectional area t■C receives the force F1, F2 with which the intestinal tract 202 is pulled. At this time, the stress σ acting on the circumferential length C of the intestinal tract 202 is expressed as follows.

$$\sigma = (F1+F2)/(t\blacksquare C) \quad \text{equation 10}$$

FIG. 12A schematically shows, by arrows, the distribution of the stress σ acting on the intestinal tract 202. The stress on the intestinal tract 202 acts on the side close to the force A and on the side close to the force F1, F2, and the forces acting on both sides are balanced. The stress σ of equation 10 is an average value in the case where it is assumed that the stress distribution is uniform on the intestinal tract 202.

For example, when the periphery of the insertion section distal end 14a is abutted on the examined body 200, the circumferential length C of the intestinal tract 202 is equal to the length of the outer periphery of the insertion section distal end 14a. When the cross section of the insertion section 14 has a circular shape with a radius r, the following equation is established.

$$C \approx 2\pi r \quad \text{equation 11}$$

Thus, from equation 10 and equation 11, the stress σ is calculated.

Hereinafter, a description will be given of the force and stress occurring in the examined body 200 in the peripheral part of the intestinal tract fixing part 208, 210, 216, which is mentioned in the above (iii). The parts where the intestinal tract 202 is fixed include the anus, the descending colon, and the ascending colon. In FIG. 11, the intestinal tract fixing parts 208 and 210 are located near the anus 206. The intestinal tract fixing part 216 is located at the descending colon. FIG. 11 shows a state in which the insertion section 14 pushes the intestinal tract 202 and the intestinal tract 202 is pulled, and thereby forces act in the intestinal tract fixing part 208 and the intestinal tract fixing part 216 near the SD-J (SD-Junction) 214, which is a boundary portion between the sigmoid colon and the descending colon.

For example, in FIG. 11, the force with which the intestinal tract 202 is pulled by the insertion section 14 is F1. At this time, with the force F acting on a part 213 of the intestinal tract 213, the part 213 moves when the intestinal tract 202 has a slack. By the movement of the intestinal tract 202 as indicated by an obliquely upwardly arrow in FIG. 11, the slack of the intestinal tract 202 decreases as indicated by a dotted line. If no hooking occurs midway, a force F3 corresponding to the force F1 acts on the intestinal tract fixing part 208. In addition, if resistance occurs midway, a force Fa, which is weaker than the force F1, acts on the intestinal tract fixing part 208 (Fa<F3). FIG. 14 shows this state.

Figure 14A:
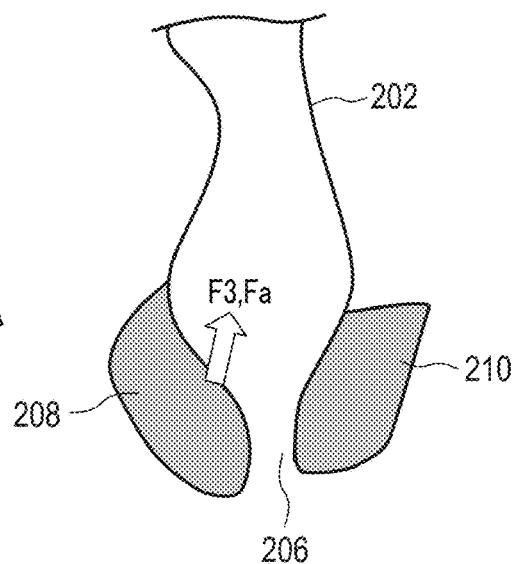
FIG. 14A is a view showing an example of force that pulls an intestinal tract fixing part.

It is assumed that the intestinal tract fixing part 208 is pulled by the force Fa in a direction of an arrow shown in FIG. 14A, i.e. substantially in a direction from the anus toward the colon. At this time, as described with reference to FIG. 12A, if the thickness of the intestinal tract 202 at the intestinal tract fixing part 208 is ta, and the length of the range in which force is applied is Ca, a stress σa in the intestinal tract fixing part 208 is expressed as follows.

$$\sigma a = Fa/(ta\blacksquare Ca) \quad \text{equation 12}$$

Figure 14B:
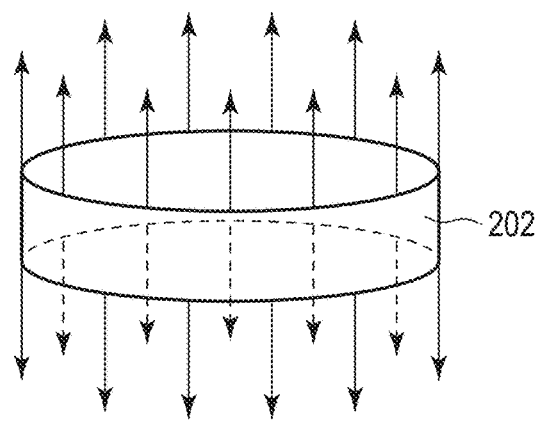
FIG. 14B is a view showing an example of a distribution of stress acting in a portion in front of the intestinal tract fixing part located near the anus.

FIG. 14B shows an example of a distribution of the stress σa acting on a part in front of the intestinal tract fixing part 208 near the anus 206. The stress on the intestinal tract 202 acts on the side close to the insertion section distal end 14a and on the side close to the intestinal tract fixing part 208 in the vicinity of the anus 206, and the forces acting on both sides are balanced. The stress σa of equation 12 is an average value in the case where it is assumed that the stress distribution is uniform on the intestinal tract 202. The stress σa is directed in two directions toward the insertion section distal end 14a that is in contact with the intestinal tract 202, and toward the intestinal tract fixing part 208 near the anus, where the intestinal tract 202 is fixed to the examined body 200.

Figure 14C:
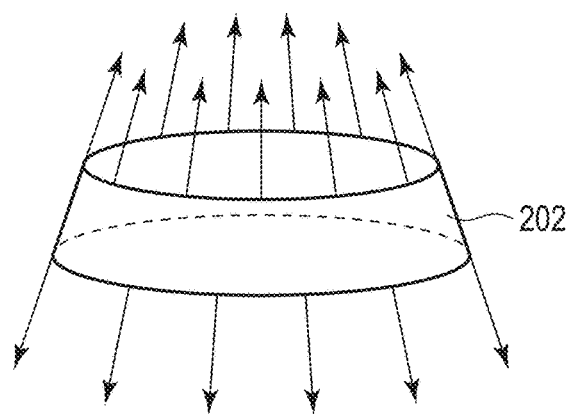
FIG. 14C is a view showing an example of a distribution of stress acting in the portion in front of the intestinal tract fixing part located near the anus.

Note that when the intestinal tract fixing part 208 near the anus extends over a relatively large range, the stress acts, with respect to a small portion near the anus of the intestinal tract 202, in a direction connecting the intestinal tract fixing part 208 near this portion and the insertion section distal end 14a. Thus, as shown in FIG. 14C, the direction of the stress σa is slightly different from the direction shown in FIG. 14B.

The stress σa is used in order to judge, in the examined body influence judgment unit 114 (to be described later), a damage that occurs or may occur in the vicinity of the anus, for example, a tear of the intestinal tract.

Hereinafter, a description will be given of a stress maximum value calculation in the second sense-of-force information calculator 108.

The stress σ acting in the vicinity of the intestinal tract may be calculated as in the above equation as a rough estimate, but, from the standpoint of safety, it is desirable to estimate a relatively large value, such as a value not greater than a certain value. Three reasons for performing the stress maximum value calculation will be stated below.

A first reason is that there is a part on which stress concentrates. For example, stress increases in enclosed areas C11 and C11 in FIG. 12A and in areas C13 and C14 shown in FIG. 13A.

A second reason is that when stress concentrates on a specific part of the intestinal tract 202, for example, as in a case of pushing the intestinal tract 202 by the insertion section distal end 12a, as shown in FIG. 12A, the range of stress, in which the same force is received, is narrowed in a part closer to the part where force is applied, i.e. the value of the circumferential length C decreases, and thus the value of the stress σ becomes greater than the value shown in equation 10.

Figure 13A:
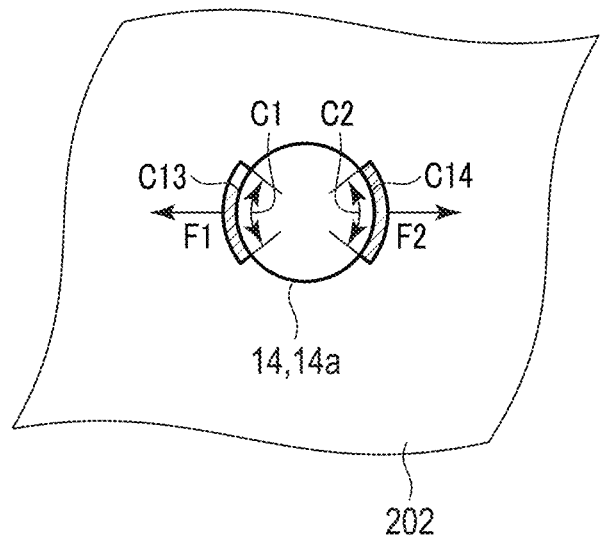
FIG. 13A is a cross-sectional view showing an example of an area where stress concentrates in the intestinal tract.

For example, as shown in FIG. 13A, when stress concentrates on a part of the intestinal tract 202, for example, an area C13, C14 existing midway between the side close to the insertion section distal end 14a and the fixing part side near the anus of the intestinal tract 202 and the SD-J, which is the inlet of the descending colon, the value of the stress becomes greater than the value of σ by equation 10. For example, when the length of the range in which the force F1 concentrates in the area C13 of the intestinal tract 202 is C1, an average value of stress σ1 acting there is expressed as follows.

$$\sigma1 = F1/(t \cdot C1) \quad \text{equation 13}$$

Similarly, when the length of the range in which the force F2 concentrates in the area C14 of the intestinal tract 202 is C2, an average value of stress σ2 acting there is expressed as follows.

$$\sigma2 = F2/(t \cdot C2) \quad \text{equation 14}$$

Figure 13B:
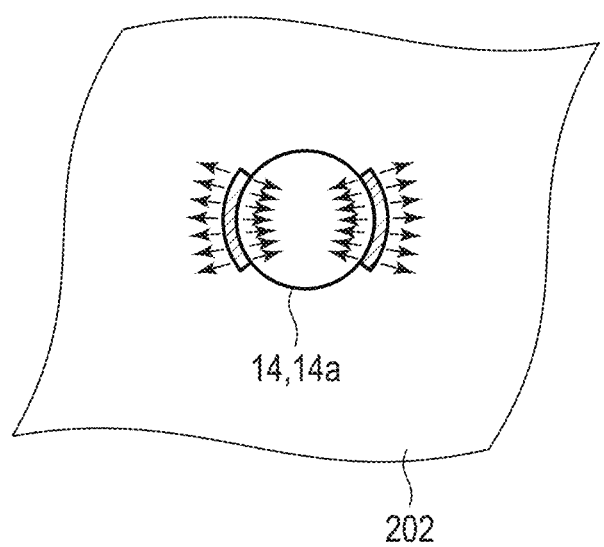
FIG. 13B is a view corresponding to FIG. 13A.

FIG. 13B shows an example of a distribution of the stresses σ1 and σ2 acting on the intestinal tract 202.

A third reason is that the external force F or the reaction force F1, F2 thereof varies with time, and may possibly take an instantaneous large value.

Taking into account the possibility of such an increase of stress, when the damage to the examined body 200, such as perforation of the lumen cavity, is considered, it is effective to multiply, for example, a safety factor, in order to estimate a maximum value of stress. The safety factor in this case may be derived by an experimental-statistical method, or by a theoretical method, or by a combination thereof. The result is expressed by an equation below.

$$\sigma = \alpha \cdot (F1+F2)/(t \cdot C) \quad \text{equation 15}$$

where α: safety factor ≥1. Thus, in equation 15, the right side of equation 10 is multiplied by the safety factor α.

As repeatedly described above, if the force or stress acting on the intestinal tract increases, there is a possibility that the patient feels a pain, or the intestinal tract is damaged. For example, a thesis "Colonic perforation and serosal tears associated with colonoscopy", Yoshiharu UNO, et al., Lancet, Jun. 28, 1997, vol. 349, No. 9069, p. 1888, describes that 3 kgf/cm² or more is a perforation risk region. In addition, a thesis "Points to be attended to for not causing accidental symptom in colonoscopy, and measures when accidental symptom occurred", Yoshiharu, UNO, and five others, Shokaki-Naishikyo ("ENDOSCOPIA DIGESTIVA"), 2000, vol. 12, No. 2, pp. 201-206, describes three cases in which a pain or perforation is mechanically caused when a tubular bend mechanism, such as an endoscope, is inserted, namely a case in which a pain or perforation is caused by a tip end of an insertion section, a case in which a pain or perforation is caused at a top portion of a stick phenomenon, and a case in which a pain or perforation is caused by a loop or an acute-angle portion. Specifically, according to the thesis, perforation occurs when the stress of the intestinal tract increases to a certain level or more, by the pressing on the intestinal tract by a tip end of the insertion section or some other acute-angle portion of an intermediate part. Further, "Jintaino Kyodo to Rouka—Seibutsu Kyojyaku Gaku niyoru Sokutei Kekka" ("Strength and Aging of Human Body—Measured Result by 'Strength of Biological Materials'"), NHK Publishing, Inc., September 1979, pp. 90-117, describes results of measurement and evaluation of tensile strength, compression strength, etc., by using test pieces obtained by cutting out portions of parts of digestive tracts of an animal and a human in strip shapes in a transverse direction. The maximum value of stress may be set by referring to such theses or the like.

Figure 15:
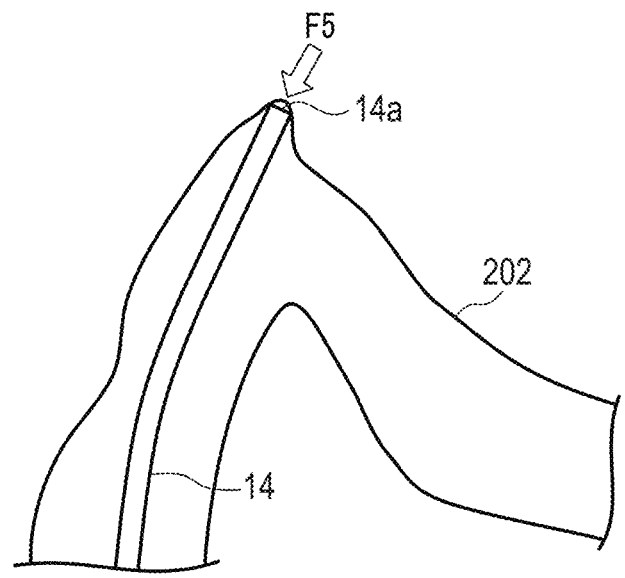
FIG. 15 is a view for describing force that the distal end of the insertion section applies to an S-shaped bend portion.
Figure 16:
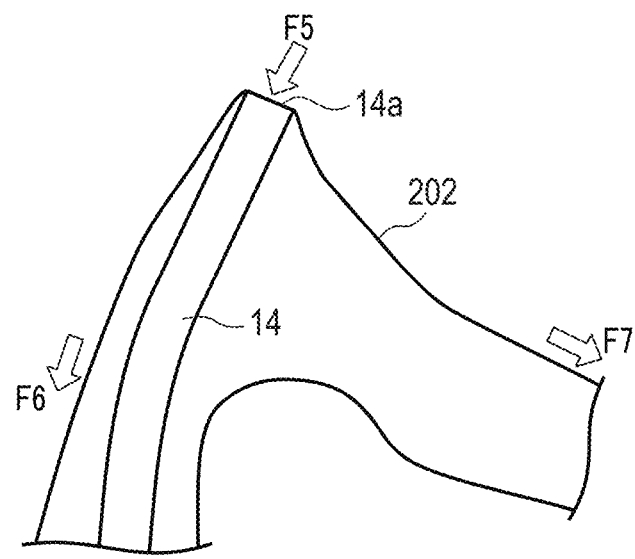
FIG. 16 is a view for describing force that the distal end of the insertion section applies to the S-shaped bend portion.
Figure 17:
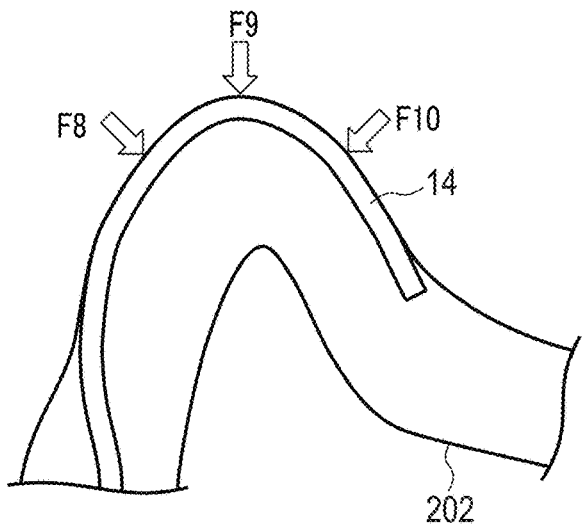
FIG. 17 is a view for describing force that an intermediate portion of the insertion section applies to the S-shaped bend portion.
Figure 18A:
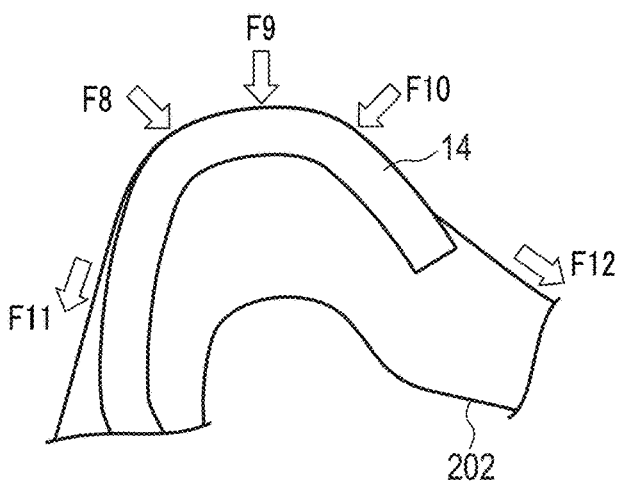
FIG. 18A is a view for describing force that an intermediate portion of the insertion section applies to the S-shaped bend portion.

Concrete examples of occurrence of stress are generally classified into two cases. One case is that the intestinal tract 202 is pushed by the insertion section distal end 14a, as shown in FIG. 15 and FIG. 16. The other case is that the intestinal tract 202 is pushed by an intermediate portion of the insertion section 14, as shown in FIG. 17 and FIG. 18A.

In FIG. 15, a periphery of the insertion section distal end 14a is in contact with the intestinal tract 202, and the insertion section distal end 14a receives a force F5 from the inner wall of the intestinal tract 202. In FIG. 16, the entirety of a distal end face of the insertion section distal end 14a is in contact with the intestinal tract 202, and the insertion section distal end 14a receives a force indicated by arrow F5 from the inner wall of the intestinal tract 202, and furthermore the intestinal tract 202 is pulled in directions indicated by arrows F6 and F7. In FIG. 17 and FIG. 18A, an intermediate portion of the insertion section 14 is in contact with the intestinal tract 202 in various contact manners, and the insertion section 14 receives forces indicated by arrows F8, F9, and F10 from the inner wall of the intestinal tract 202 at contact parts. In FIG. 18A, furthermore, the intestinal tract 202 is pulled in directions indicated by arrows F11 and F12.

A large difference between the case of pushing the intestinal tract 202 by the insertion section distal end 14a and the case of pushing the intestinal tract 202 by the intermediate portion of the insertion section 14 is the manner of contact between the insertion section 14 and the intestinal tract 202. Hereinafter, the calculation of the stress σ in these two cases will be described.

(Calculation of Stress by Distal Portion)

The case of pushing the intestinal tract 202 by the insertion section distal end 14a will be described. When the force, which acts on the insertion section 14 from the inside or surface of the examined body, acts on the insertion section distal end 14a, the stress is calculated by using the contact state including the shape of the insertion section distal end 14a and an angle θ between the direction of the insertion section distal end 14a and the direction of application of the force. If θ1=θ2 in FIG. 12A, the stress σ is distributed as shown in FIG. 12A. In the same setting as in equation 10, the circumferential length C of the intestinal tract 202, the stress σ of which is calculated, is 2 πr, assuming that the cross section of the insertion section distal end 14a is a circle with a radius r. Since a length perpendicular to the direction in which the stress acts is 2 r, it can be thought that the forces F1 and F2 as described with reference to FIG. 12A to FIG. 12C acts in the width of 2 r. At this time, the stress σ is expressed as follows.

$$\sigma = \alpha \cdot F/(t \cdot 2r \cdot |\cos \theta|) \quad \text{equation 16}$$

Here, t is the thickness of the intestinal tract 202, like equation 10; α is the safety factor, like equation 15; θ is the above-described angle; and F is the force with which the insertion section 14 pushes the intestinal tract 202.

A supplementary description will be given of the relationship between equation 10 and equation 16. The forces acting in a specific range of the intestinal tract, like the intestinal tract 202 shown in FIG. 12A, are outward forces F1 and F2, and the force, which is balanced with the forces F1 and F2, occurs from F. Conversely, if the force F is considered as a reference, the forces F1 and F2 are as follows, when the angles between the forces F1 and F2 and the force F are θ1 and θ2.

$$F1 = \alpha \cdot F/|\cos \theta1|$$

$$F2 = (1-\alpha)F/|\cos \theta2|$$

When θ1=θ2=θ, the following is established.

$$F1+F2 = F/|\cos \theta|$$

Using these equations, equation 16 can be derived from equation 10.

When the directions and magnitudes of the two forces, with which the intestinal tract 202 is pulled, are not uniform, each force may be calculated. In particular, by considering the greater one of the two forces, it is possible to assume the damage to the examined body 200, and to implement measures or the like.

(Calculation of Stress by Intermediate Portion)

The case of pushing the intestinal tract 202 by the intermediate portion of the insertion section 14 will be described. When the force, which acts on the insertion section 14, acts on the intermediate portion in the longitudinal direction of the insertion section 14, the stress is calculated by using the contact state including the cross-sectional shape of the insertion section 14 in the vicinity of the position of application of the force, and an angle θ between the center axis direction of the insertion section 14 and the direction of application of the force.

When the intestinal tract 202 is pushed by the intermediate portion of the insertion section 14, the stress σ, which acts on the part of the circumferential length C of the intestinal tract 202, is expressed as follows, assuming that the stress σ acts uniformly on the part of the circumferential length C.

$$\sigma = \alpha \cdot F / (t \cdot C \cdot |\cos\theta|) \quad \text{equation 17}$$

Here, t is the thickness of the intestinal tract 202, like equation 10; α is the safety factor, like equation 15; θ is the above-described angle; and F is the force with which the insertion section 14 pushes the intestinal tract 202.

The circumferential length C of the intestinal tract 202, the stress σ of which is calculated, may take various shapes, depending on the cross-sectional shape or bend shape of the insertion section 14 and the direction in which the intestinal tract 202 is pulled. Thus, in order to conduct detailed studies, examinations corresponding to individual situations are necessary. Here, with respect to an example of the shape, a study is conducted by simplification.

Figure 18B:
FIG. 18B is a view showing an example of a cross section of an intestinal tract.

As shown in FIG. 18B, it is assumed that the cross-sectional shape of the insertion section 14 is a circle with a radius r, and the length in a minor axis direction of the part of the circumferential length C of the intestinal tract 202 is 2 r. For example, it is assumed that the shape of the circumferential length C is an elliptic shape. It is assumed that the length in a major axis direction of the circumferential length C of the intestinal tract 202 is L, and the part of the circumferential length C is an elliptic shape with a minor axis 2 r and a major axis L. At this time, the circumferential length C is expressed as follows, by using r and L.

$$C = 4a \int_0^{\pi/2} \sqrt{1 - \frac{L^2}{4r^2} \cdot \sin^2 t}\, dt \approx \pi\left(r + \frac{L}{2}\right)\left(1 + \frac{3\left(\frac{L-2r}{L+2r}\right)^2}{10 + \sqrt{4 - 3\left(\frac{L-2r}{L+2r}\right)^2}}\right) \quad \text{equation 18}$$

Like the case of the calculation of the stress by the insertion section distal end 14a, when the directions and magnitudes of the two forces, with which the intestinal tract 202 is pulled, are not uniform, each force may be calculated. In particular, by considering the greater one of the two forces, it is possible to assume the damage to the examined body 200, and to implement measures or the like.

In the above manner, the second sense-of-force information calculator 108 calculates, as the second sense-of-force information relating to the force or stress occurring in the lumen cavity of the examined body 200, the stress occurring in the inside or on the surface of the examined body 200 by the abutment of the insertion section distal end 14a or the intermediate portion of the insertion section 14.

(Contact State Estimation Unit)

The contact state estimation unit 112 estimates the contact state between the insertion section 14 and the examined body 200. As described above, when the second sense-of-force information is calculated, in particular, when the stress information is calculated, the information relating to how the insertion section 14 is in contact with the lumen cavity of the examined body 200, for example, the circumferential length C of the intestinal tract, which is used at a time of calculating the stress, is necessary. For example, in order to assume/calculate the circumferential length C, the contact state estimation unit 112 estimates how the insertion section 14 is in contact with the lumen cavity of the examined body 200. In other words, the contact state estimation unit 112 estimates, as a contact area estimation unit, the length of the outer periphery of a contact area that is an area in which the flexible member 12 and the examined body 200 are in contact with each other, and sets the contact area as a stress estimation area, i.e. a target area for estimating stress.

Figure 19:
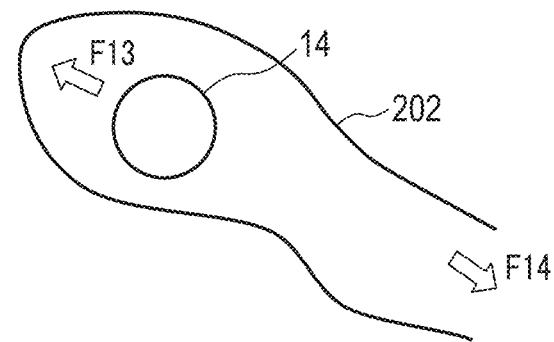
FIG. 19 is a view showing an example in a case where the distal end of the insertion section is in contact with the intestinal tract is viewed from above the endoscope.
Figure 20:
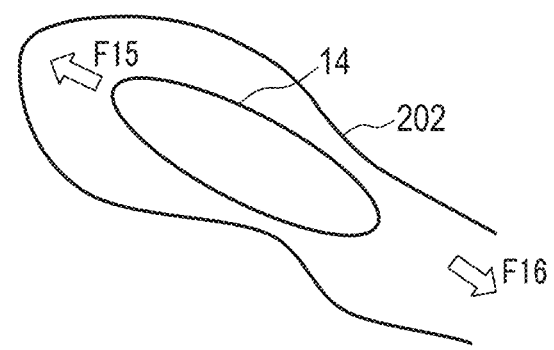
FIG. 20 is a view showing an example in a case where a state in which the intermediate portion of the insertion section is in contact with the intestinal tract is viewed from above the endoscope.

Examples of the contact state are shown in FIG. 19 and FIG. 20. FIG. 19 shows an example of a cross section in a case where an example of the state in which the insertion section distal end 14a is in contact with the intestinal tract 202 is viewed from above the endoscope. A force F13, which acts on the intestinal tract 202 and with which the intestinal tract 202 is pulled to the cecum side, and a force F14, which acts on the intestinal tract 202 and with which the intestinal tract 202 is pulled to the anus side, are conceptually shown. FIG. 20 shows an example of a cross section in a case where an example of the state in which the intermediate portion of the insertion section 14 is in contact with the intestinal tract 202 is viewed from above the endoscope. A force F15, which acts on the intestinal tract 202 and with which the intestinal tract 202 is pulled to the cecum side, and a force F16, which acts on the intestinal tract 202 and with which the intestinal tract 202 is pulled to the anus side, are conceptually shown. The insertion section distal end 14a and insertion section 14 shown in the Figures are in contact with the intestinal wall of the intestinal tract 202.

The contact state estimation unit 112 estimates the contact state, based on the disposition and shape of the insertion section 14 in the lumen cavity of the examined body 200. Since the ultimate object is to calculate the stress relating to the second sense-of-force information in the second sense-of-force information calculator 108, the contact state estimation unit 112 estimates the contact state including also the thickness of the lumen cavity at the contact part.

In the estimation of the contact state, it is possible to use a predetermined or patterned contact state, or to use predetermined values corresponding to physical features such as the body height, body weight, abdominal circumference, age, gender, etc., or to perform a calculation at each time. For example, the contact state between the insertion section 14 and the examined body 200 can be estimated by using the same disposition and shape of the insertion section 14 in the lumen cavity of the examined body 200, as used in the examined body information estimation unit 110. Since the contact state of the intermediate portion varies depending on the bend state, i.e. curvature, a value may be set for each curvature, or a function may be set by using the curvature as one variable.

(Examined Body Influence Judgment Unit)

The examined body influence judgment unit 114 acquires the second sense-of-force information from the second sense-of-force information calculator 108. The examined body influence judgment unit 114 judges the influence on the examined body 200, based on the second sense-of-force information and a criterion. Examples of concrete judgment contents in the examined body influence judgment unit 114 are the presence/absence of damage such as a pain caused in the examined body 200, tear, breakage or perforation, and the degree of the content of damage.

For example, it is assumed that the intestinal tract fixing part 208 is pulled in the direction of θa with force Fa. At this time, it is considered that two or more damages occur at the same time, for example, among such damages as tear of the intestinal tract 202, tear of the intestinal tract fixing part 208, ablation between the intestinal tract 202 and the intestinal tract fixing part 208, and the like. The examined body influence judgment unit 114 judges, by using a combination of (Fa, θa) as an input, the above-described damage in the intestinal tract fixing part 208, 210 near the anus 206, or other possible damage, such as ablation between the intestinal tract and fixing part.

In addition, when damage is judged from the stress σa per unit area, the examined body influence judgment unit 114 judges, by using the stress σa expressed by equation 12 as an input, damage that occurs or may occur near the anus 206, for example, tear of the intestinal tract 202.

It is assumed that the criterion in the examined body influence judgment unit 114 is set by gathering relations between inputs and judgment results, based on experience, experimental results, simulation results, etc.

Although the manner of judging the influence on the examined body at the anus was described, a similar judgment manner is applicable to parts other than the anus.

The intestinal tract is fixed to the body near the anus, the descending colon, and the ascending colon. Thus, depending on the part where the insertion section pushes the intestinal tract, the values of θ1 and θ2 described with reference to, for example, FIG. 12 vary. Here, since the disposition of the intestinal tract depends on the body shape, for example, the body height, the abdominal circumference, the degree of obesity, or the length of the intestines, the estimation and calculation based on the body shape are necessary. In addition, as regards the value of the thickness t and the degree of influence, since the age and gender also have relations, the influence on the examined body need to be judge by considering such conditions as the examined body information. Specifically, also in the judgment in the examined body influence judgment unit 114, it is useful to use the examined body information by the examined body information estimation unit 110.

For example, which organ is influenced by the pressure p described with reference to the above equation 6 and equation 7, or, in other words, which organ is pushed, can be judged from the shape and disposition of the insertion section 14 in the examined body, the anatomical disposition of the examined body, a combination thereof, the variation of forces, and the like. For example, the cross-sectional area S of equation 6 depends mainly on the shape of the part on which the insertion section 14 or insertion section distal end 14a is abutted. If the manners of abutment are classified into types or patterns, the cross-sectional area S can be regarded as being constant for each pattern, and the influence on the examined body, such as damage or pain, can be judged with respect to each manner of abutment, based on the force F in place of the pressure S.

The examined body influence judgment unit 114 sends to the information output unit 116 the influence judgment information relating to the judgment of the presence/absence, content, and degree of damage to the examined body, which are based on the criterion.

(Information Output Unit)

The information output unit 116 outputs to the outside of the control apparatus 100 the output information including the second sense-of-force information and the influence judgment information. In addition, the information output unit 116 sends the output information to the output information storage unit 118.

(Output Information Storage Unit)

The output information storage unit 118 stores the output information from the information output unit 116. The output information is the information that is also output to an information presentation device 140. The output information storage unit 118 may also store the shape and disposition information calculated by the shape and disposition information calculator 102, time instants, elapsed times, etc. By the storage, it becomes possible to confirm situations at an occurrence location of stress and at an occurrence location in the insertion section 14 at a time of occurrence of stress.

(Information Presentation Device)

The information presentation device 140 acquires, through the information output unit 116, at least one of the second sense-of-force information acquired from the second sense-of-force information calculator 108 and the influence judgment information acquired from the examined body influence judgment unit 114. The information presentation device 140 presents, as needed, information processed to be suitable for presentation to a surgeon or the like, based on at least one of the second sense-of-force information and the influence judgment information, or both of the second sense-of-force information and the influence judgment information.

The information presentation device 140 may be, for example, at least one of a display including a monitor screen, such as a liquid crystal display, an audio device, and a vibration device and an electric stimulation device provided in the operation unit 16 of the endoscope 10. Specifically, the information presentation device 140 may be a visual presentation device, an audio presentation device, or a tactile presentation device, or a combination thereof. If the display is taken as an example, output methods are characters, signs, figures, and images. As regards these devices and methods, two or more of them may be used at the same time, or the devices and methods may be switched in accordance with the sense-of-force information and the degree of the influence judgment result.

FIG. 21 is a view schematically showing another example of the main configuration of a sense-of-force evaluation system 1a according to the first embodiment. Hereinafter, the sense-of-force evaluation system 1a will be described with respect to only the different points between the sense-of-force evaluation system 1a and the sense-of-force evaluation system 1.

The sense-of-force evaluation system 1a includes an endoscope system 2a and a control apparatus 100a. The endoscope system 2a includes an endoscope 10a. The endoscope 10a includes a driving mechanism 44. The control apparatus 100a includes a feedback circuit 120, a feedback information storage unit 122, and a driving circuit 124, in place of the information output unit 116, output information storage unit 118, and information presentation device 140 of the sense-of-force evaluation system 1. In the endoscope system 2a, it is presupposed that a part of the driving system of the insertion section 14 is motor-driven/automated.

Note that the sense-of-force evaluation system 1a may include the information output unit 116, output information storage unit 118, and information presentation device 140.

(Driving Mechanism)

The operation unit 16 of the endoscope 10a may include at least a part of the driving mechanism 44. The driving mechanism 44 includes a driving system such as a motor. The driving mechanism 44 applies driving force to the insertion section 14, thereby changing at least one of the bend shape and the position of the insertion section 14. In this manner, the endoscope 10a is a motor-driven endoscope, at least a part of the driving system of which is motor-driven, or an automatic insertion endoscope.

(Feedback Circuit and Driving Circuit)

The feedback circuit 120 provides, as needed, to the driving circuit 124 driving control information processed to be suitable for feedback to the driving mechanism 44 of the insertion section 14, based on at least one of the second sense-of-force information acquired from the second sense-of-force information calculator 108 and the influence judgment information acquired from the examined body influence judgment unit 114. Based on the feedback information or the like, the driving circuit 124 operates the driving mechanism 44.

(Feedback Information Storage Unit)

The feedback information storage unit 122 stores at least one of the fed-back second sense-of-force information, influence judgment information, and driving control information. These pieces of information are the information that is also output to the feedback circuit 120. The feedback information storage unit 122 may also store the shape and disposition information calculated by the shape and disposition information calculator 102, time instants, elapsed times, etc. By the storage, it becomes possible to confirm situations at an occurrence location of stress and at an occurrence location in the insertion section 14 at a time of occurrence of stress.

(Sense-of-force Evaluation Flow)

Figure 22:
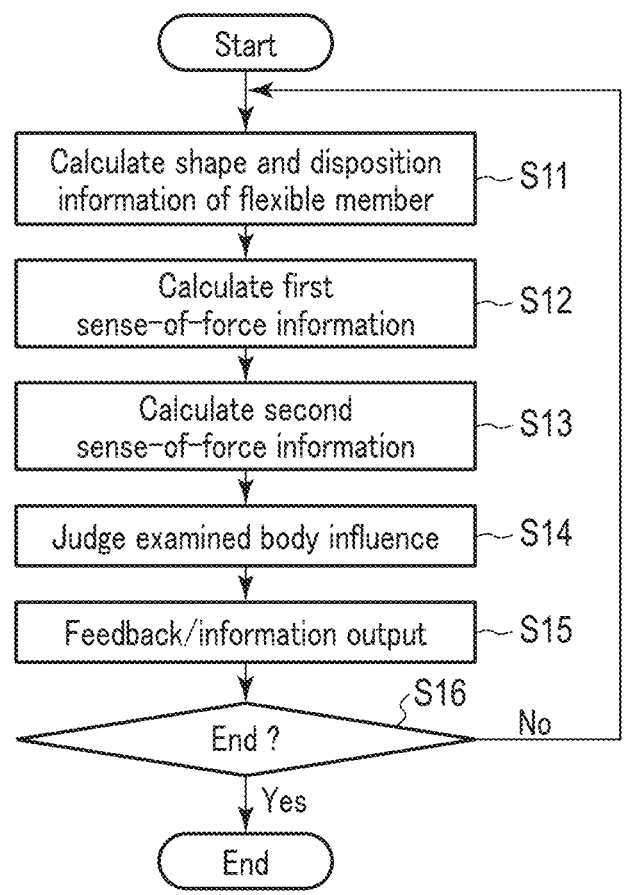
FIG. 22 is a view showing an example of a process by the sense-of-force evaluation system according to the first embodiment.

FIG. 22 shows an example of a process flow by the sense-of-force evaluation system 1 or 1a. For example, the sense-of-force evaluation system 1 or 1a may prepare in a memory a software program for causing the processor of the control apparatus 100 or 100a to function as all or a part of the above-described parts, and the processor may execute the program, and thereby the processor may achieve at least some functions of the above-described parts. Hereinafter an example of the process by the processor will be described.

In step S11, the sense-of-force evaluation system 1 or 1a calculates the shape and disposition information of the insertion section 14 or flexible member 12. In step S12, the sense-of-force evaluation system 1 or 1a calculates the first sense-of-force information relating to the force acting on the insertion section 14, based on the shape and disposition information acquired in step S11. In step S13, the sense-of-force evaluation system 1 or 1a calculates the second sense-of-force information relating to the force or stress occurring in the lumen cavity of the examined body 200. In step S14, the sense-of-force evaluation system 1 or 1a judges the influence that the examined body receives/may receive. In step S15, the sense-of-force evaluation system 1 outputs the information. Alternatively, the sense-of-force evaluation system 1a feeds the information based on the second sense-of-force information/influence judgment information back to the driving mechanism 44.

In step S16, the sense-of-force evaluation system 1 or 1a determines whether or not to finish the process. If it is determined that the process is not to be finished (step S16—No), the process returns to step S11, and the process from step S11 is repeated. If it is determined that the process is to be finished (step S16—Yes), the process is finished.

By this process, only the disposition or deformation of the insertion section 14, which is the flexible member 12, is detected. Thereby, the sense-of-force information occurring in the lumen cavity of the examined body can efficiently be evaluated without directly measuring the force or stress.

For example, there is an attempt to directly measure the force or pressure as the influence that the endoscope causes to the examined body. There is a method using a device such as a pressure sensor, in order to detect the pressure. However, if the pressure acting on the surface of a tubular bend mechanism is to be detected over a wide range, many sensors need to be disposed near the surface. Consequently, there is a high possibility that the outside diameter of the tubular bend mechanism increases in order to secure the space for disposing the sensors or wiring lines, and the cost for members or the cost for implementation increases. In addition, such a method is conceivable that force is detected by using devices such as an electrical sensor, for instance, a tactile sensor configured to detect force, a strain gauge, a pressure-sensitive resistor, or electrically-driven rubber, or a photoelectric sensor, for instance, an optical fiber, or force, i.e., pressure, acting per unit area is detected from the detected force and the area on which the force is applied. However, even if the force acting on the part with which the sensor is in contact is understood, the force occurring in the inside of the examined body that is the target may not be calculated, or the information necessary for calculating the pressure from the force, e.g. the shape of the tubular bend mechanism, may not be obtained. Further, even if the pressure under a specific condition can be calculated, the pressure may not be calculated when the shape of the tubular bend mechanism changes or the position of application of force changes, and there is a possibility that the precision considerably lowers.

By contrast, according to the present embodiment, the second sense-of-force information relating to the force or stress occurring due to the force acting in the inside of the examined body or on the surface outside of the examined body, in particular, the information of the stress in the outer periphery of the stress estimation area, can be calculated without direct measurement. In the present embodiment, a force sensor or a stress sensor, which directly measures the measured body, is not necessary, and saving in space is achieved. For example, reduction in diameter of the insertion section 14, which is the flexible member 12, is possible.

Additionally, the sense-of-force evaluation system 1 can enhance the precision of detection of force and stress by estimating and calculating, from the examined body information, the information of the force acting on the examined body, and by estimating the stress acting in the inside of the examined body or acting on the surface outside the examined body.

Additionally, in the sense-of-force evaluation system 1, the maximum value of force and stress, or the upper-limit value, which the maximum value can take, can be calculated. Thereby, it becomes easier to estimate damage occurring in the inside of the examined body or on the surface outside the examined body.

Additionally, the sense-of-force evaluation system 1 includes the contact state estimation unit 112 functioning as the contract area estimation unit, which estimates the contact state, e.g. the contact area, between the flexible member 12 and the examined body 200. In order to estimate the stress acting in the lumen cavity of the examined body from the information of the force acting on the examined body, it is necessary to assume or estimate the contact state between the flexible member and the inside of the examined body or the surface outside the body. By estimating the contact state at each time, the detection precision of stress can be enhanced.

The distal end of the flexible member, such as the insertion section distal end 14a, is one of parts that cause damage to the inside or outside of the examined body, such as causing perforation in the intestinal tract or the like. When the insertion section 14 deviates from the insertion path, or when the insertion section 14 is hooked in the inside of the examined body such as the intestinal tract or on the surface outside the body, the contact state is estimated based on the insertion state of the distal end of the flexible member, for example, the shape, disposition in the body, force information, and the shape and disposition information of the inside of the examined body or of the surface outside the body, and thereby the detection precision of the force and stress can be enhanced.

Additionally, in the present embodiment, the value of the mechanical characteristic of the flexible member 12, which is stored in the mechanical characteristic storage unit 106, is acquired by the first sense-of-force information calculator 104. Thereby, the detection of force acting on the flexible member 12 can be performed by a simple method, and there is no need to increase the diameter of the flexible member 12 by providing a sensor, and there can be provided the sense-of-force evaluation system having a practical force and stress detection function, while being capable of performing real-time detection.

Additionally, in the present embodiment, the examined body information, which is estimated by the examined body information estimation unit 110, is acquired by the second sense-of-force information calculator 108. Thereby, since the degree of influence on the function of the examined body is understood, it becomes possible to judge whether or not to suspend the operation, or whether or not to release the operation, i.e. whether or not to put back the operation, or whether or not to continue the operation. It is also possible to judge whether or not to perform a predetermined treatment on the examined body, based on the force or stress estimated to have occurred.

Additionally, at least either the information of force and stress or the information indicative of the degree of influence on the examined body is provided to the operator by the information presentation device 140. Thereby, the operator can examine and judge measures as needed, and the operator can continue a safe operation by the operator, suspend an operation with a problem, or return from a state with a problem.

Additionally, at least either the information of force and stress or the information indicative of the degree of influence on the examined body is provided to the driving mechanism 44 by the feedback circuit 120, and the driving is performed to set the force and stress at a certain value or less. Thereby, it becomes possible to continue the safe driving or the operation by the driving mechanism 44, to suspend the driving or the operation with a problem, or to return from a state with a problem.

First Embodiment: Modifications

FIG. 23 is a view schematically showing an example of the main configuration of a sense-of-force evaluation system 1b according to a modification of the first embodiment. FIG. 24 is a view schematically showing an example of the main configuration of a sense-of-force evaluation system 1c according to a modification of the first embodiment. Hereinafter, the sense-of-force evaluation system 1b will be described with respect to only the different point between the sense-of-force evaluation system 1b and the sense-of-force evaluation system 1. The sense-of-force evaluation system is will be described with respect to only the different point between the sense-of-force evaluation system 1c and the sense-of-force evaluation system 1a.

The different point between the sense-of-force evaluation system 1b and the sense-of-force evaluation system 1 is the presence/absence of a sense-of-force generation judgment unit 126. The sense-of-force evaluation system 1b includes the sense-of-force generation judgment unit 126 in a control apparatus 100b. Similarly, the different point between the sense-of-force evaluation system 1c and the sense-of-force evaluation system 1a is the presence/absence of the sense-of-force generation judgment unit 126. The sense-of-force evaluation system 1c includes the sense-of-force generation judgment unit 126 in a control apparatus 100c. Hereinafter, the sense-of-force generation judgment unit 126 will be described.

(Sense-of-force Generation Judgment Unit)

The sense-of-force generation judgment unit 126 acquires the shape and disposition information of the insertion section 14 from the shape and disposition information calculator 102. Based on the shape and disposition information of the insertion section 14, the sense-of-force generation judgment unit 126 judges whether or not force occurs in the lumen cavity of the examined body 200.

For example, when the information section 14 is in a stage before insertion into the examined body, or in a state in which erroneous detection occurs in the position detection or sense-of-force detection, the sense-of-force generation judgment unit 126 judges that no sense-of-force occurs. The stage before insertion can be judged from the spatial positional relationship between the examined body, in particular, the anus or intestinal tract, which is the inlet of insertion, and the distal end of the insertion section 14. In addition, in the position detection or sense-of-force detection, since the insertion operation speed is about several cm/second on average, it is not considered that a sudden large value of sense-of-force occurs, and when a large value occurs due to such position detection error or sense-of-force detection error, erroneous detection can be judged to some extent. Similarly, when sense-of-force occurs, if the value of sense-of-force greatly varies in a short time, the possibility of erroneous detection can be considered.

The judgment result by the sense-of-force generation judgment unit 126 is sent to the contact state estimation unit 112.

According to the present modifications, there can be provided the sense-of-force evaluation system 1b, 1c that detects the sense-of-force information relating to the force or stress occurring in the lumen cavity of the examined body, with the detection precision of the contact state or sense-of-force information being enhanced by the judgment by the sense-of-force generation judgment unit 126.

Second Embodiment

A second embodiment of the present invention will be described with reference to FIG. 25 to FIG. 28. In the second embodiment, the same structural elements as in the first embodiment are denoted by the same reference signs as in the first embodiment, and a description thereof is omitted, and the different points from the first embodiment will mainly be described.

In the second embodiment, the sense-of-force evaluation system id includes a working manipulator 300 as an insertion apparatus. The sense-of-force evaluation system 1*d* includes a working system 2*d*. The working system 2*d* includes the working manipulator 300 and a main body 302. The working manipulator 300 includes, as flexible members, a first working arm 304, a second working arm 306, and an observation arm 308. The arms 304, 306, and 308 are inserted into the examined body 200. The main body 302 includes a control apparatus 100*d*.

Concrete examples of the working manipulator include a medical manipulator and an industrial manipulator. However, the purposes of use are not limited to these.

The medical manipulator is assumed to perform grasping, cutting, resection, burying of a device or the like, suture, administration of a medicine, disinfection, cleaning, etc., by a medical arm, while observing a predetermined part by an observation arm. The examined body is assumed to be a human, an animal, a vegetable, etc. The predetermined part is a body cavity or a cut-and-opened body part as a main location for a purpose of use, but the location for the purpose of use is not limited, and the location for the purpose of use may be a body surface. If an observation system is separately provided, the observation arm is not necessarily required. In addition, a plurality of observation arms may be provided in order to simultaneously observe a plurality of locations, to ensure a view field, or to generate a 3D image. The observation arm or the medical arm may be a combination of an elastic body and a bendable section such as an endoscope insertion section, or a manipulator that is flexible by one or more joints, or a combination thereof, or may include a rigid arm as one of arms.

The industrial manipulator is assumed to be mainly used for inspections and maintenance of devices, piping, structures, and the like. The industrial manipulator is used for works in parts, buildings, and areas where a person cannot enter because of sizes and environments, and the industrial manipulator is intended to perform works that persons cannot do. The examined body is a device, piping, a structure, an area, etc., and these are work targets. The industrial manipulator includes one or more working arms and, where necessary, one or more observation arms.

The purposes of use of the sense-of-force evaluation system 1*d* are a precise work that cannot be performed by a person's hand, a work of simultaneously performing many operations, a work at a location to which a person's hand cannot reach because the person's hand does not have enough length or is too large, a difficult work for a person, and a work in an environment involving danger.

Figure 25:
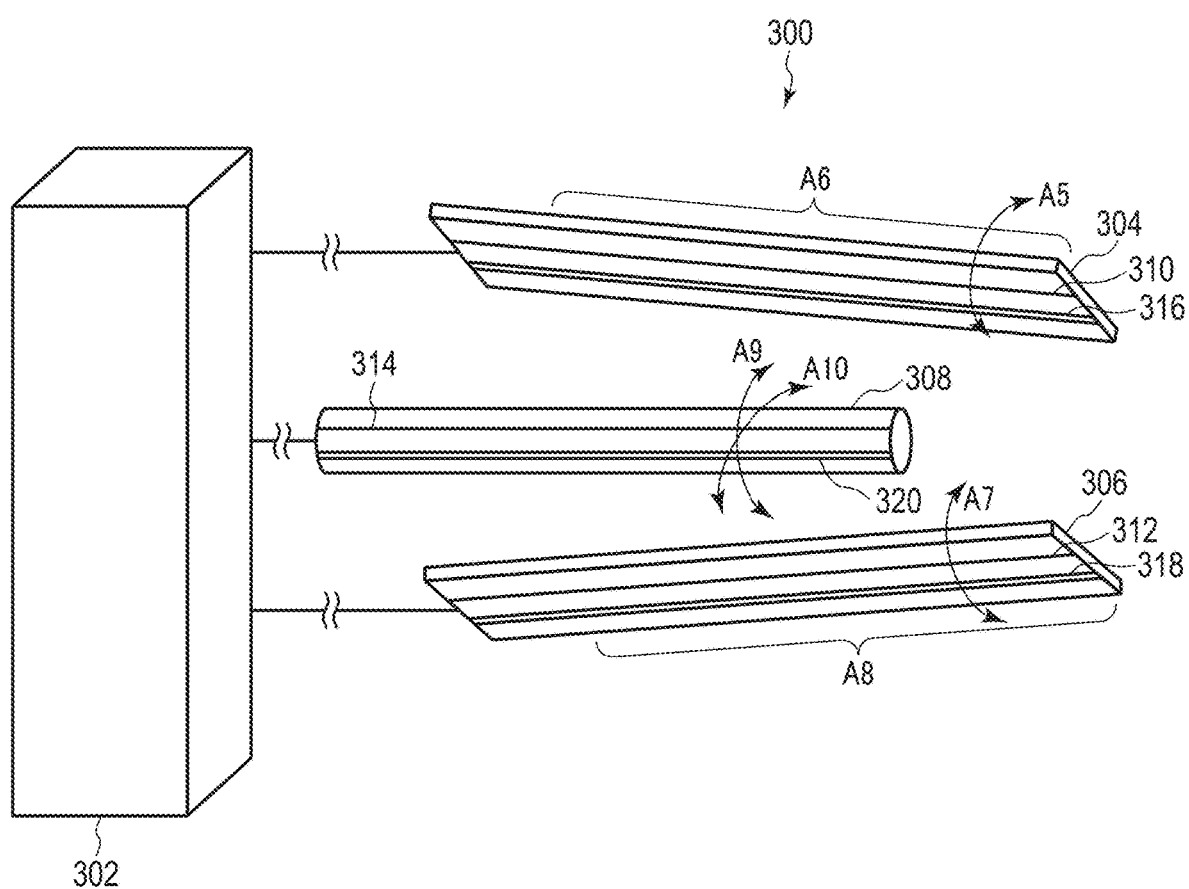
FIG. 25 is a view schematically showing an example of a configuration of a working system in a sense-of-force evaluation system according to a second embodiment.

In the working manipulator 300, the first working arm 304, second working arm 306, and observation arm 308 extend from the main body 302. The first working arm 304 and second working arm 306 have, for example, thin flat plate shapes. For example, each of the first working arm 304 and second working arm 306 has a rectangular shape, with lengths a and b of sides of the cross section thereof being a<<b, and a length c in the longitudinal direction of each of the first working arm 304 and second working arm 306 being a<<b<<c. Each of the first working arm 304 and second working arm 306 bends mainly in a direction substantially perpendicular to a side surface with the width b, i.e. moves in such a manner that the bend direction is limited to one direction. In FIG. 25, since the directions of movement of the first working arm 304 and second working arm 306 are limited, it is possible to concentrate on an operation in the movable direction, and to perform a stable work and a precise work.

The first working arm 304 and second working arm 306 grasp articles, or perform works such as processing and assembly. A working tool corresponding to the purpose of use may be attached, as needed, to the distal end of each arm 304, 306. The working tool may not necessarily be attached, or may be a replaceable one.

The observation arm 308 is an elongated arm having a substantially circular transverse cross section. The observation arm 308 includes an illumination optical system, an observation optical system, and an imaging element, which are built in a distal end of the observation arm 308. When the distal ends of the first working arm 304 and second working arm 306 perform work on a target, the observation arm 308 varies the bend shape thereof, thus enabling observation of the target in various directions.

Shape sensors 310, 312, and 314 and four wires 316, 318, and 320 are assembled in the first working arm 304, second working arm 306 and the observation arm 308, respectively. Note that since two operation wires are provided on a front surface and two wires are provided on a back surface of each of the arms 304, 306, and 308, FIG. 25 shows only two operation wires of each of the arms 304, 306, and 308.

The positions and shapes of the arms 304, 306, and 308 are detected by the shape sensors 310, 312, and 314, respectively. The shape sensors 310, 312, and 314 may be configured like the shape sensor 50 described in the first embodiment. In addition, the arms 304, 306, and 308 can actively perform bend operations by the operation wires 316, 318, and 320, respectively. In FIG. 25, a bend direction of the first working arm 304 is indicated by A5, and a bendable range thereof is indicated by A6. In addition, a bend direction of the second working arm 306 is indicated by A7, and a bendable range thereof is indicated by A8. Further, bend directions of the observation arm 308 are indicated by A9 and A10. Note that, aside from the shape sensor 310, 312, 314, a detection mechanism capable of detecting the position and shape of the arm 304, 306, 308 may be adopted. Aside from the operation wires 304, 306, 308, an operation mechanism capable of bend-operating the arm 304, 306, 308 may be adopted.

It is assumed that the flexural rigidity in a predetermined range of each of the first working arm 304, second working arm 306, and observation arm 308 is understood. When the flexural rigidity varies depending on the position in the longitudinal direction and depending on the bend direction, it is assumed that the distribution of the flexural rigidity in the longitudinal direction is understood with respect to each of necessary bend directions.

When work is performed on the examined body 200 by using the first working arm 304, second working arm 306, and observation arm 308, if the arm 304, 306, 308 comes in contact with the examined body 200, force acts on the examined body 200 and also force acts on the arm 304, 306, 308 from the examined body 200. In addition, if the arms come in contact with each other, the arms apply force to each other. It is assumed that which arm is in contact with which arm is judged from the relation of positions and shapes of the arms.

At this time, the force applied from the examined body 200 to the working arm 304, 306 and observation arm 308 can be calculated as a reaction force of the resultant force of the forces applied to the examined body. The resultant force of the forces applied to the examined body 200 can be calculated by an optimization method, based on the fact that the bending moment, which is calculated from the bend state by expressing the flexural rigidity and bend amount in three dimensions in the equation of the bending moment expressed in equation 3, and by substituting the result of equation 5b into an evaluation expression, is balanced with the bending moment occurring by external force. However, when no force occurs in the bend direction and the direction perpendicular to the longitudinal direction, the measurement of the position and shape and the calculation of force may be simplified and performed as appropriate.

Individual forces occurring in the examined body from the resultant force applied to the examined body 200 can be calculated by recognizing the structure of the examined body 200 in the same manner as in the first embodiment. The advantageous effects, which are thereby obtained, are the same as in the first embodiment.

Figure 27:
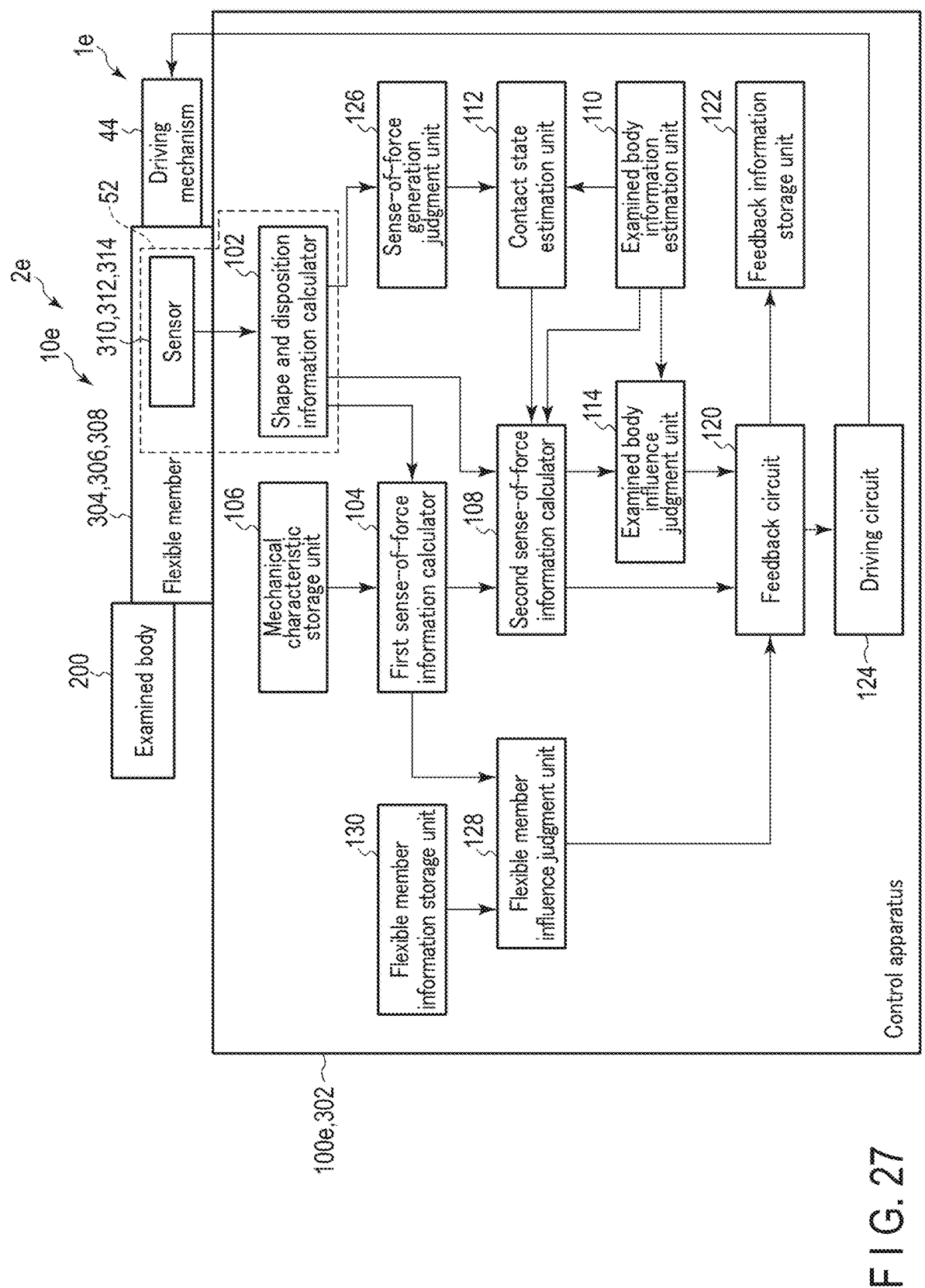
FIG. 27 is a view schematically showing another example of the main configuration of the sense-of-force evaluation system according to the second embodiment.

FIG. 26 is a view schematically showing an example of the main configuration of the sense-of-force evaluation system 1d according to the second embodiment. FIG. 27 is a view schematically showing an example of the main configuration of a sense-of-force evaluation system 1e according to the second embodiment. Hereinafter, the sense-of-force evaluation system 1d will be described with respect to only the different point between the sense-of-force evaluation system 1d and the sense-of-force evaluation system 1b. The sense-of-force evaluation system 1e will be described with respect to only the different point between the sense-of-force evaluation system 1e and the sense-of-force evaluation system 1c.

The different point between the sense-of-force evaluation system 1d according to the second embodiment and the sense-of-force evaluation system 1b according to the modification of the first embodiment is the presence/absence of a flexible member influence judgment unit 128 and a flexible member information storage unit 130. The sense-of-force evaluation system 1d includes the flexible member influence judgment unit 128 and flexible member information storage unit 130 in a control apparatus 100d. Similarly, the different point between the sense-of-force evaluation system 1e and the sense-of-force evaluation system is is the presence/absence of the flexible member influence judgment unit 128 and flexible member information storage unit 130. The sense-of-force evaluation system 1e includes the flexible member influence judgment unit 128 and flexible member information storage unit 130 in a control apparatus 100e. Hereinafter, the flexible member influence judgment unit 128 and flexible member information storage unit 130 will be described.

(Flexible Member Information Storage Unit)

The flexible member information storage unit 130 stores flexible member information that is information relating to the first working arm 304, second working arm 306, and observation arm 308, which are flexible members. The flexible member information may be values relating to mechanical characteristics and physical or chemical characteristics of the arms 304, 306, and 308 that are flexible members, and include, for example, values of flexural rigidities of the first working arm 304, second working arm 306, and observation arm 308, as described above.

(Flexible Member Influence Judgment Unit)

The flexible member influence judgment unit 128 judges the influence on the arms 304, 306, and 308 by collating the sense-of-force information relating to the force or stress acting on the flexible members, with a criterion based on the arms 304, 306, and 308 that are flexible members. Concrete judgment contents include the presence/absence, content and degree of damage caused to the flexible members, such as breakage of the members, degradation of rigidity or operability, and shortening of product life, and the necessity of maintenance, urgency, etc.

Note that in the present embodiment, the working system 2d composed of the three arms was described, but the number of arms may be freely chosen. For example, in a working system including only one working arm, observation may be performed by the naked eye or through a microscope that is separately provided. In addition, three working arms and three observation arms may be provided, and work may be performed while one part is being viewed in multiple directions, or works on plural parts may be performed simultaneously or successively. With the provision of the plural working arms and plural observation arms, the examined body can be separated into parts and observation and work can be performed on these parts, or a plurality of examined bodies can be inteagrated, e.g. assembled, and injection or the like can be performed. Each of the working arm and the observation arm may have a changeable function, or may have a plurality of functions at the same time.

As regards works, a person may operate the movement of the arms or may operate works on the spot or from a remote place, or a person may only instruct the contents of operations.

Like the first embodiment, as a modification, the sense-of-force evaluation system id may include a control apparatus 100d including the information output unit 116 and output information storage unit 118, as shown in FIG. 26. In addition, the sense-of-force evaluation system 1e may include a control apparatus 100e including the feedback circuit 120, feedback information storage unit 122, and driving circuit 124, as shown in FIG. 27.

(Sense-of-force Evaluation Flow)

Figure 28:
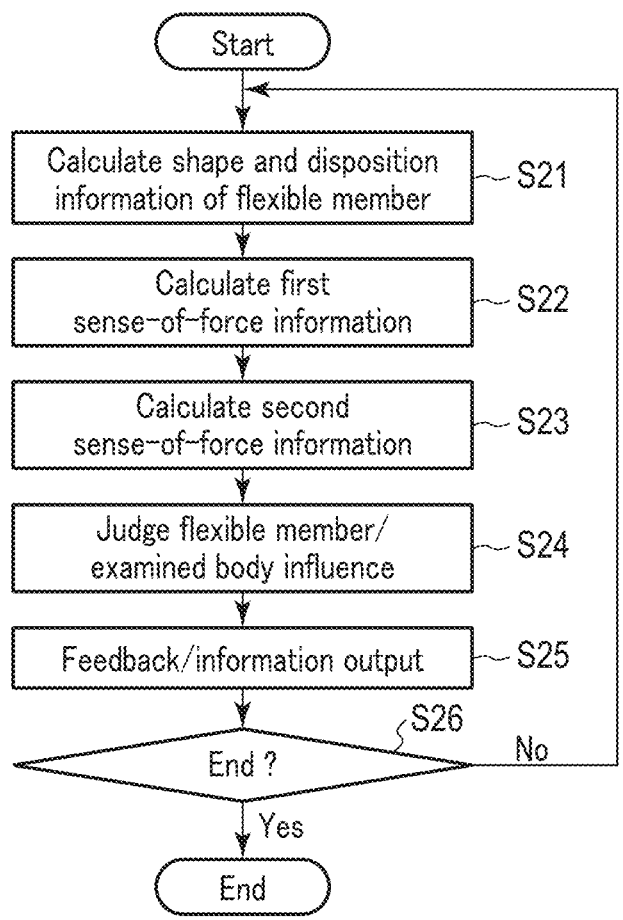
FIG. 28 is a view showing an example of a process by the sense-of-force evaluation system according to the second embodiment.

FIG. 28 is a view showing an example of a process flow by the sense-of-force evaluation system 1d or 1e. For example, the sense-of-force evaluation system 1d or 1e may prepare in a memory a software program for causing the processor of the control apparatus 100d or 100e to function as all or a part of the above-described parts, and the processor may execute the program, and thereby the processor may achieve at least some functions of the above-described parts. Hereinafter an example of the process by the processor will be described.

In step S21, the sense-of-force evaluation system 1d, 1e calculates the shape and disposition information of the arms 304, 306, and 308 that are flexible members. In step S22, the sense-of-force evaluation system 1d, 1e calculates the first sense-of-force information relating to the force acting on the arms 304, 306, and 308, based on the shape and disposition information acquired in step S21. In step S23, the sense-of-force evaluation system 1d, 1e calculates the second sense-of-force information relating to the force or stress occurring in the lumen cavity of the examined body 200. In step S24, the sense-of-force evaluation system 1d, 1e judges the influence that the flexible members receive/may receive, and the influence that the examined body receives/may receive. In step S25, the sense-of-force evaluation system 1d outputs the information. Alternatively, the sense-of-force evaluation system 1e feeds the information based on the second sense-of-force information/influence judgment back to the driving mechanism 44.

In step S26, the sense-of-force evaluation system 1d, 1e determines whether or not to finish the process. If it is determined that the process is not to be finished (step S26—No), the process returns to step S21, and the process from step S21 is repeated. If it is determined that the process is to be finished (step S26—Yes), the process is finished.

According to the second embodiment, by the flexible member influence judgment unit 128, it is possible to understand the degree of influence on the functions of the arms 304, 306, and 308 that are flexible members, the influence being received from the examined body, operator, other devices, equipment, and the environment of use such as the location of installation. Thereby, it is possible to judge whether or not to suspend the operation, or whether or not to release the operation, i.e. whether or not to put back the operation, or whether or not to continue the operation. It is also possible to judge whether or not to perform a predetermined treatment, such as repair or component replacement, on the arms 304, 306, and 308, based on the force or stress estimated to have occurred in the arms 304, 306, and 308. For example, it is possible to prevent the arms 304, 306, and 308 from being damaged or destroyed by the force from the examined body.

As described above, according to each embodiment of the present invention, there can be provided the sense-of-force evaluation systems 1, 1a, 1b, 1c, 1d, and 1e and the sense-of-force evaluation apparatuses 100, 100a, 100b, 100c, 100d, and 100e, which can precisely and easily acquire the sense-of-force information relating to the force or stress occurring the measured body. According to the sense-of-force evaluation systems and the sense-of-force evaluation apparatuses, the information relating to the bend shape of the flexible member and the force with which the flexible member pushes the examined body can be acquired, and the force or stress acting on the examined body can be detected from the information such as the cross-sectional shape and bend shape of the insertion section at the position where the force acts. In other words, the force and stress acting on the examined body can be estimated by taking into account various forces acting in the examined body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stress estimation system comprising:
a flexible member with flexibility, the flexible member being configured to be inserted into an inside of an examined body and to apply force to an inner surface of the examined body;
one or more processors, each comprising hardware, the one or more processors being configured to:
acquire force information relating to force acting on the flexible member;
calculate information of stress relating to a stress estimation area, based on the force information;
acquire examined body information including a length of an outer periphery of the stress estimation area and a thickness of the examined body in the stress estimation area,
calculate a magnitude and a direction of force acting on the examined body in the stress estimation area, and to calculate the information of the stress, based on the calculated magnitude and direction of the force, the length of the outer periphery of the stress estimation area, and the thickness of the examined body; and
when force acting on the flexible member acts on an intermediate portion in a longitudinal direction of the flexible member, calculate the information of the stress by using a cross-sectional shape of the flexible member in a vicinity of a position where the force acts, and an angle formed between a center axis direction of the flexible member and a direction of application of the force.

2. The stress estimation system of claim 1, wherein the one or more processors being further configured to estimate a length of an outer periphery of a contact area that is an area in which the examined body and the flexible member are in contact with each other, and to set the contact area as the stress estimation area.

3. The stress estimation system of claim 1, wherein the one or more processors being configured to set an area of a fixing part where the examined body is fixed to a structure outside the examined body as the stress estimation area.

4. The stress estimation system of claim 1, wherein the calculating of the information of the stress comprises using a safety factor.

5. The stress estimation system of claim 1, wherein when force acting on the flexible member from an inside or a surface of the examined body acts on a distal portion of the flexible member, the the one or more processors being configured to calculate the information of the stress by using a shape of the distal portion and an angle formed between the center axis direction and the direction of application of the force.

6. The stress estimation system of claim 1, wherein the one or more processors being further configured to estimate the examined body information.

7. The stress estimation system of claim 6, further comprising a shape and disposition information detection unit sensors configured to detect shape and disposition information relating to a shape and a disposition of the flexible member, and
wherein the one or more processors being configured to estimate the examined body information, based on the detected shape and disposition information.

8. The stress estimation system of claim 7, wherein the one or more processors being further configured to:
acquire mechanical characteristic information indicative of mechanical characteristics at positions in a longitudinal direction of the flexible member; and
calculate force information relating to force acting on the flexible member,
wherein the shape and disposition information includes information of a deformation state at the positions, and
the one or more processors being further configured to calculate the force information relating to force acting on one or more positions of the flexible member, based on the information of the deformation state and the mechanical characteristic information at the positions in the longitudinal direction of the flexible member.

9. The stress estimation system of claim 1, wherein the one or more processors being further configured to judge an influence that the information of the calculated stress exerts on the examined body.

10. The stress estimation system of claim 1, further comprising an information presentation device configured to provide presentation information to a user based on the information of the stress.

11. The stress estimation system of claim 1, further comprising:
a motor configured to cause, by driving force, a change in a shape and a position of the flexible member;
wherein the one or more processors being configured to feed driving information based on the information of the stress back to the motor.

12. The stress estimation system of claim 1, wherein the one or more processors being further configured to judge an influence that the force information exerts on the flexible member.

13. A stress estimation apparatus comprising:
one or more processors, each comprising hardware, the one or more processors being configured to:
    acquire force information relating to force acting on a flexible member configured to apply force to an inner surface of an examined body;
    calculate information of stress relating to a stress estimation area, based on the force information;
    acquire examined body information including a length of an outer periphery of the stress estimation area and a thickness of the examined body in the stress estimation area,
    calculate a magnitude and a direction of force acting on the examined body in the stress estimation area, and to calculate the information of the stress, based on the calculated magnitude and direction of the force, the length of the outer periphery of the stress estimation area, and the thickness of the examined body; and
    when force acting on the flexible member acts on an intermediate portion in a longitudinal direction of the flexible member, calculate the information of the stress by using a cross-sectional shape of the flexible member in a vicinity of a position where the force acts, and an angle formed between a center axis direction of the flexible member and a direction of application of the force.

14. An endoscope system comprising:
an endoscope insertion section with flexibility, the endoscope insertion section configured to be inserted into an inside of an examined body and to apply force to an inner surface of the examined body;
one or more processors, each comprising hardware, the one or more processors being configured to:
    acquire force information relating to force acting on the endoscope insertion section;
    calculate information of stress relating to a stress estimation area, based on the force information;
    acquire examined body information including a length of an outer periphery of the stress estimation area and a thickness of the examined body in the stress estimation area,
    calculate a magnitude and a direction of force acting on the examined body in the stress estimation area, and to calculate the information of the stress, based on the calculated magnitude and direction of the force, the length of the outer periphery of the stress estimation area, and the thickness of the examined body; and
    when force acting on the flexible member acts on an intermediate portion in a longitudinal direction of the flexible member, calculate the information of the stress by using a cross-sectional shape of the flexible member in a vicinity of a position where the force acts, and an angle formed between a center axis direction of the flexible member and a direction of application of the force.

15. A stress estimation method comprising:
acquiring force information relating to force acting on a flexible member to apply force to an inner surface of an examined body;
calculating information of stress relating to a stress estimation area, based on the force information;
acquiring examined body information including a length of an outer periphery of the stress estimation area and a thickness of the examined body in the stress estimation area,
calculating a magnitude and a direction of force acting on the examined body in the stress estimation area, and to calculate the information of the stress, based on the calculated magnitude and direction of the force, the length of the outer periphery of the stress estimation area, and the thickness of the examined body; and
when force acting on the flexible member acts on an intermediate portion in a longitudinal direction of the flexible member, calculating the information of the stress by using a cross-sectional shape of the flexible member in a vicinity of a position where the force acts, and an angle formed between a center axis direction of the flexible member and a direction of application of the force.

16. The stress estimation apparatus of claim 13, wherein the flexible member is an endoscope insertion section.

* * * * *